United States Patent
Wong et al.

(10) Patent No.: US 8,541,413 B2
(45) Date of Patent: Sep. 24, 2013

(54) SUSTAINED RELEASE EYE DROP FORMULATIONS

(75) Inventors: Vernon G. Wong, Menlo Park, CA (US); Louis L. Wood, Potomac, MD (US)

(73) Assignee: Ramscor, Inc., Menlo Park, CA (US)

( * ) Notice: Subject to any disclaimer, the term of this patent is extended or adjusted under 35 U.S.C. 154(b) by 471 days.

(21) Appl. No.: 12/236,877

(22) Filed: Sep. 24, 2008

(65) Prior Publication Data

US 2009/0136445 A1    May 28, 2009

Related U.S. Application Data

(63) Continuation-in-part of application No. 11/826,833, filed on Jul. 18, 2007, now abandoned, which is a continuation-in-part of application No. 11/236,426, filed on Sep. 27, 2005, now Pat. No. 7,906,136.

(60) Provisional application No. 60/709,665, filed on Aug. 19, 2005, provisional application No. 60/614,484, filed on Oct. 1, 2004, provisional application No. 60/831,991, filed on Jul. 19, 2006, provisional application No. 60/690,315, filed on Jun. 14, 2005.

(51) Int. Cl.
*A61K 31/535* (2006.01)

(52) U.S. Cl.
USPC .................. 514/235.8; 514/912; 514/913

(58) Field of Classification Search
None
See application file for complete search history.

(56) References Cited

U.S. PATENT DOCUMENTS

| | | | |
|---|---|---|---|
| 4,304,765 A | 12/1981 | Shell et al. | |
| 4,309,996 A | 1/1982 | Theeuwes | |
| 4,310,543 A * | 1/1982 | Gallo-Torres et al. | 514/530 |
| 4,551,332 A * | 11/1985 | Stillman | 424/401 |
| 4,568,547 A | 2/1986 | Herschler | |
| 4,728,721 A | 3/1988 | Yamamoto et al. | |
| 4,804,539 A * | 2/1989 | Guo et al. | 424/450 |
| 4,839,342 A * | 6/1989 | Kaswan | 424/450 |
| 4,849,228 A | 7/1989 | Yamamoto et al. | |
| 4,853,224 A | 8/1989 | Wong | |
| 4,997,652 A | 3/1991 | Wong | |
| 5,164,188 A | 11/1992 | Wong | |
| 5,283,236 A * | 2/1994 | Chiou | 424/94.61 |
| 5,371,078 A | 12/1994 | Clark et al. | |
| 5,443,505 A | 8/1995 | Wong et al. | |
| 5,472,703 A * | 12/1995 | Vanderlaan et al. | 424/429 |
| 5,520,927 A * | 5/1996 | Kim et al. | 424/450 |
| 5,620,700 A | 4/1997 | Berggren et al. | |
| 5,632,984 A | 5/1997 | Wong et al. | |
| 5,653,992 A | 8/1997 | Bezwada et al. | |
| 5,760,075 A * | 6/1998 | Stjernschantz et al. | 514/530 |
| 5,766,242 A | 6/1998 | Wong et al. | |
| 5,767,153 A * | 6/1998 | Bowman et al. | 514/530 |
| 5,770,589 A | 6/1998 | Billson et al. | |
| 5,824,072 A | 10/1998 | Wong | |
| 5,869,079 A | 2/1999 | Wong et al. | |
| 5,886,030 A * | 3/1999 | Maniar | 514/458 |
| 5,945,115 A | 8/1999 | Dunn et al. | |
| 5,945,121 A * | 8/1999 | Kato et al. | 424/450 |
| 6,130,200 A | 10/2000 | Brodbeck et al. | |
| 6,174,540 B1 | 1/2001 | Williams et al. | |
| 6,214,838 B1 | 4/2001 | Sohda et al. | |
| 6,331,311 B1 | 12/2001 | Brodbeck et al. | |
| 6,331,313 B1 | 12/2001 | Wong et al. | |
| 6,369,116 B1 | 4/2002 | Wong et al. | |
| 6,429,226 B1 * | 8/2002 | Stjernschantz et al. | 514/530 |
| 6,468,961 B1 | 10/2002 | Brodbeck et al. | |
| 6,534,089 B1 * | 3/2003 | Ayer et al. | 424/473 |
| 6,537,566 B1 | 3/2003 | Copeland et al. | |
| 6,653,288 B1 | 11/2003 | Beuvry et al. | |
| 6,699,493 B2 | 3/2004 | Wong | |
| 6,726,918 B1 | 4/2004 | Wong et al. | |
| 6,733,786 B1 | 5/2004 | Kim et al. | |
| 6,827,931 B1 | 12/2004 | Donovan | |
| 6,855,340 B2 | 2/2005 | Brewer | |
| 7,074,426 B2 | 7/2006 | Kochinke | |
| 7,618,651 B2 * | 11/2009 | Murthy | 424/488 |
| 2002/0064547 A1 | 5/2002 | Chern et al. | |
| 2003/0044467 A1 | 3/2003 | Brodbeck et al. | |
| 2003/0108626 A1 * | 6/2003 | Benita et al. | 424/731 |
| 2003/0119832 A1 * | 6/2003 | Goldblum | 514/237.5 |
| 2003/0211123 A1 * | 11/2003 | Shukla et al. | 424/400 |
| 2003/0216303 A1 | 11/2003 | Ambuhl et al. | |
| 2004/0092435 A1 | 5/2004 | Peyman | |
| 2004/0106914 A1 | 6/2004 | Coppeta et al. | |
| 2004/0151753 A1 | 8/2004 | Chen et al. | |
| 2004/0151754 A1 | 8/2004 | Ashton | |
| 2005/0101517 A1 | 5/2005 | De Nijs et al. | |
| 2005/0118206 A1 | 6/2005 | Luk et al. | |
| 2005/0143363 A1 | 6/2005 | De Juan et al. | |
| 2005/0244469 A1 | 11/2005 | Whitcup et al. | |

FOREIGN PATENT DOCUMENTS

| | | |
|---|---|---|
| CA | 2 436 361 A1 | 8/2002 |
| WO | 99/65916 A1 | 12/1999 |
| WO | WO 00/02554 A1 * | 1/2000 |
| WO | 00/59488 A2 | 10/2000 |
| WO | 00/71163 A1 | 11/2000 |
| WO | 01/70256 A1 | 9/2001 |
| WO | 03/099223 A2 | 12/2003 |
| WO | WO 2004/011054 A2 | 2/2004 |
| WO | WO 2004/081196 A2 | 9/2004 |

OTHER PUBLICATIONS da Rocha et al. Current Opinion inn Pharmacology 2001 1:364-369.*
Parrish et al. American Journal of Ophthalmology 2003 135:688-703.*
Coleman et al., 37(12) J. Pharm. Pharmacol. 878-83 (1985).
Fishman et al., 27(7) Invest. Ophthalmol. Vis. Sci. 1103-06 (1986).
Migally, 2(4) Arch. Androl. 365-69 (1979).
Wang et al., 90 J. Cont. Release 345-54 (2003).
Supplementary European Search Report dated Aug. 13, 2009.

* cited by examiner

*Primary Examiner* — Juliet Switzer
*Assistant Examiner* — Caralynne Helm
(74) *Attorney, Agent, or Firm* — Baker & Hostetler LLP

(57) ABSTRACT

This invention provides for biocompatible, biodegradable eye drop pharmaceutical formulations useful for the treatment of ocular indications. In particular, tocopherols and their esters of low water solubility, notably α-tocopheryl acetate, are exceptional vehicles for biocompatible, nonirritating topical eye drop formulations that provide sustained release of active agents.

6 Claims, 7 Drawing Sheets

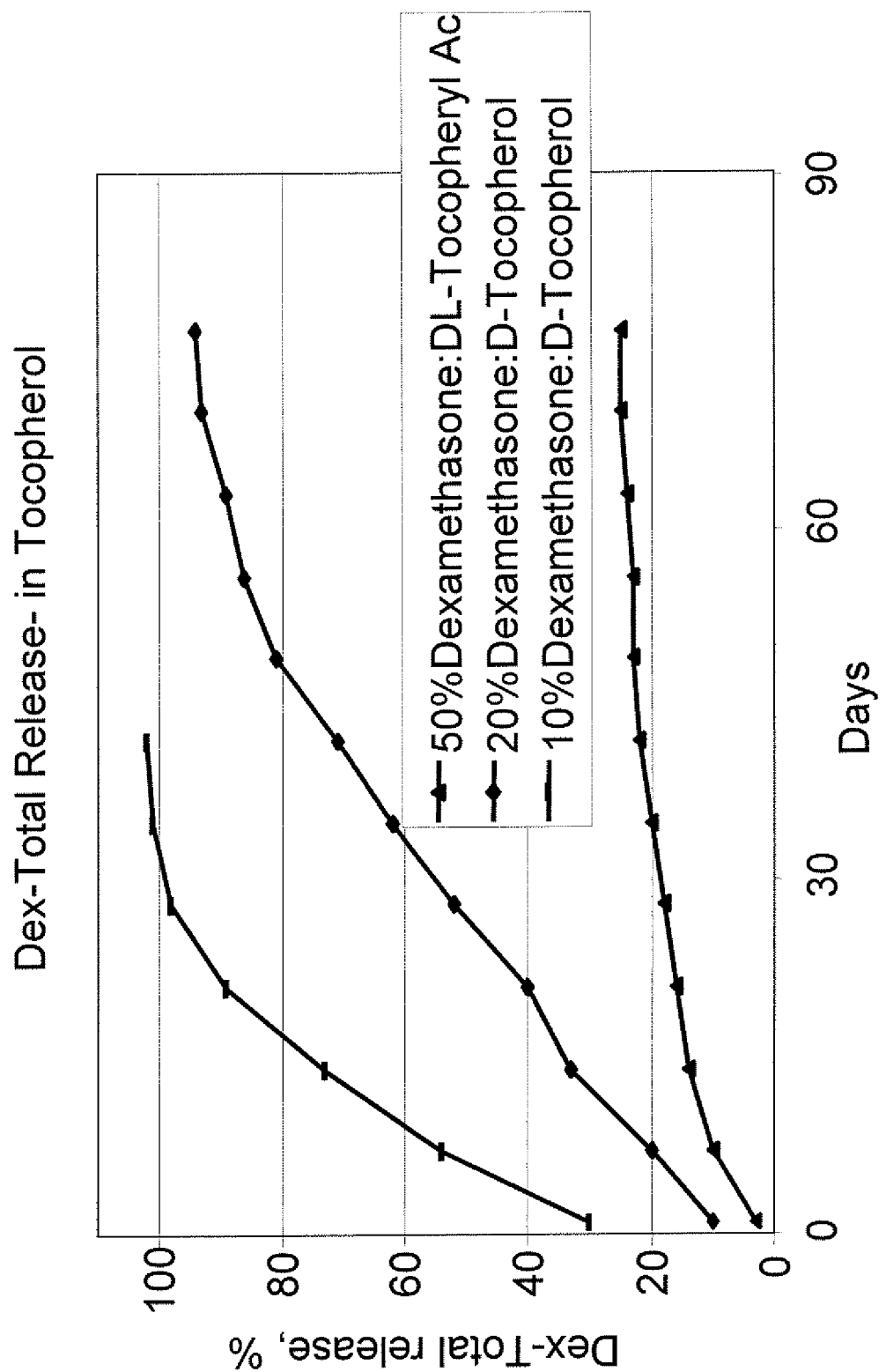

SUSTAINED RELEASE EYE DROP FORMULATIONS

RELATED APPLICATIONS

This application claims the benefit under 35 U.S.C. §119 (e) of U.S. patent application Ser. No. 60/690,315, filed Sep. 25, 2007, entitled Sustained Release Eye Drops and Conveniently Implantable Sustained Release Drug Formulations, by Vernon G. Wong and Louis L. Wood, and is a continuation-in-part of U.S. patent application Ser. No. 11/826,833, filed Jul. 17, 2007, which claims the benefit under 35 U.S.C. §119 (e) of U.S. patent application Ser. No. 60/831,991, filed Jul. 19, 2006, which is a continuation-in-part and claims the benefit under 35 U.S.C. §120 of U.S. patent application Ser. No. 11/236,426, filed Sep. 27, 2005, which is related to and claims the benefit under 35 U.S.C. §119(e) of U.S. patent application Ser. No. 60/709,665, filed Aug. 19, 2005, and Ser. No. 60/614,484, filed Oct. 1, 2004, each entitled Conveniently Implantable Sustained Release Drug Compositions, by Vernon G. Wong and Louis L. Wood. Each of the foregoing applications is incorporated in its entirety herein.

FIELD OF THE INVENTION

The present invention relates to the field of ophthalmology involving biocompatible, biodegradable, sustained-release formulations of beneficial, active agents for topical administration to the eye.

BACKGROUND OF THE INVENTION

Current topical eye drop formulations, in addition to often eliciting some degree of transient irritation, provide only short term exposure of beneficial agents to the eye and thus often require several administrations daily. Other modes of drug delivery, such as oral delivery and injection, may result in high and low blood concentrations and/or shortened half-life in the blood, in addition to systemic delivery of medicaments that are only required in the eye. In some cases, achieving therapeutic efficacy with these standard administrations requires large doses of medications that may result in toxic side effects. Additionally, some eye drop formulations are unstable over the normal period of treatment, which may be exacerbated by patient mis-handling. The technologies relating to controlled drug release have been attempted in an effort to circumvent some of the pitfalls of conventional therapy. Their aims are to deliver medications on a continuous and sustained manner.

There remains a need for a more economical, practical, and efficient way of producing and manufacturing drug delivery systems that may be used locally, in liquid, gel, or ointment formulations. In particular, there remains a need for sustained-release formulations for topical administrations (eye drops) of beneficial, active agents to the eye.

SUMMARY OF THE INVENTION

An object of the present invention provides for economical, practical, and efficient drug delivery systems. According to the present invention, this drug delivery system is produced easily, delivered easily to the site of indication, and is both biocompatible and biodegradable. In other words, the biocompatible, biodegradable formulations of the present invention disappear harmlessly after delivering active agent to the desired site. The formulations of the present invention provide for novel therapies that are easily used by qualified medical practitioners as well as by subjects in need thereof. The formulations deliver therapeutic and non-toxic levels of active agents over the desired extended time frame, often primarily at the site of administration.

The embodiments of the present invention provide for formulations for topical administrations of active agents to the eye. The present invention provides for eye drop formulations comprising at least one active agent in a biocompatible, biodegradable excipient that sustains the release of the active agent, and which may be chosen from tocopherol isomers and/or their esters; and tocotrienols and/or their esters, such as d, l and dl isomers of $\alpha$, $\beta$, $\delta$, $\epsilon$, $\eta$ tocopherols and similar isomers of the tocotrienols and the esters of these tocopherols and tocotrienols with straight and branched chain C2 to C20 aliphatic acids, or their esters of C3 to C20 straight chain dicarboxylic acids; the mono, di, and tri esters of O-acetylcitric acid or O-propionylcitric acid or O-butyrylcitric acid with C1 to C10 straight and branched chain aliphatic alcohols; the mono, di, and tri esters of citric acid with C1 to C10 straight and branched chain aliphatic alcohols. In another embodiment of the invention, the active agent or excipient may be an omega-3 fatty acid or an ester thereof Another embodiment of the present invention provides for a formulation comprising a nonpolymeric, biodegradable, bioabsorbable excipient and the active agent is one or more antioxidants, either alone or included with one or more steroids and/or quinolone anti-infectives. Typically, the formulations of the present invention provide for the sustained release of the active agent for at least four days.

The active agent envisioned in an embodiment of the present invention is at least one agent of the analgesics, anesthetics, narcotics, angiostatic steroids, anti-inflammatory steroids, angiogenesis inhibitors, nonsteroidal anti-inflammatories, anti-infective agents, antibiotics, antifungals, antivirals, alpha androgenergic agonists, beta adrenergic blocking agents, carbonic anhydrase inhibitors, mast cell stabilizers, miotics, prostaglandins, antihistamines, antimicrotubule agents, antineoplastic agents, antipoptotics, aldose reductase inhibitors, antihypertensives, antioxidants, growth factor agonists and antagonists, vitrectomy agents, adenosine receptor antagonists, adenosine deaminase inhibitors, glycosylation antagonists, anti-aging peptides, topoisemerase inhibitors, anti-metabolites, alkylating agents, oncogene activation inhibitors, telomerase inhibitors, antibodies or portions thereof, fusion proteins, tyrosine kinase inhibitors, ribonucleotide reductase inhibitors, cytotoxins, IL2 therapeutics, neurotensin antagonists, peripheral sigma ligands, endothelin ETA/receptor antagonists, antihyperglycemics, anti-glaucoma agents, anti-chromatin modifying enzymes, insulins, glucagon-like-peptides, immunosuppressive agents, tissue repair agents, essential fatty acids, and nucleic acids such as antisense oligonucleotides, siRNA or RNAi.

In another aspect of the present invention, more than one biodegradable, biocompatible excipient may be used to facilitate sustained release of an active agent. For example, a relatively small amount of a tocopherol, such as $\alpha$ tocopheryl acetate, may be added to a mixture of omega-3 fatty acid and prednisolone, increasing the sustained release of prednisolone from the formulation.

In particular embodiments, the eye drop formulation consists of $\alpha$ tocopheryl acetate and cyclosporin A, rapamycin, or timolol, or a prostaglandin. In another embodiment of the invention, the eye drop formulation consists of $\alpha$ tocopheryl acetate and latanoprost.

BRIEF DESCRIPTION OF THE DRAWINGS

FIG. 4 depicts Dex release from two different formulations of Dex:d-tocopherol and one formulation of Dex:dl-tocopherol acetate.

DETAILED DESCRIPTION OF THE INVENTION

Figure 1:
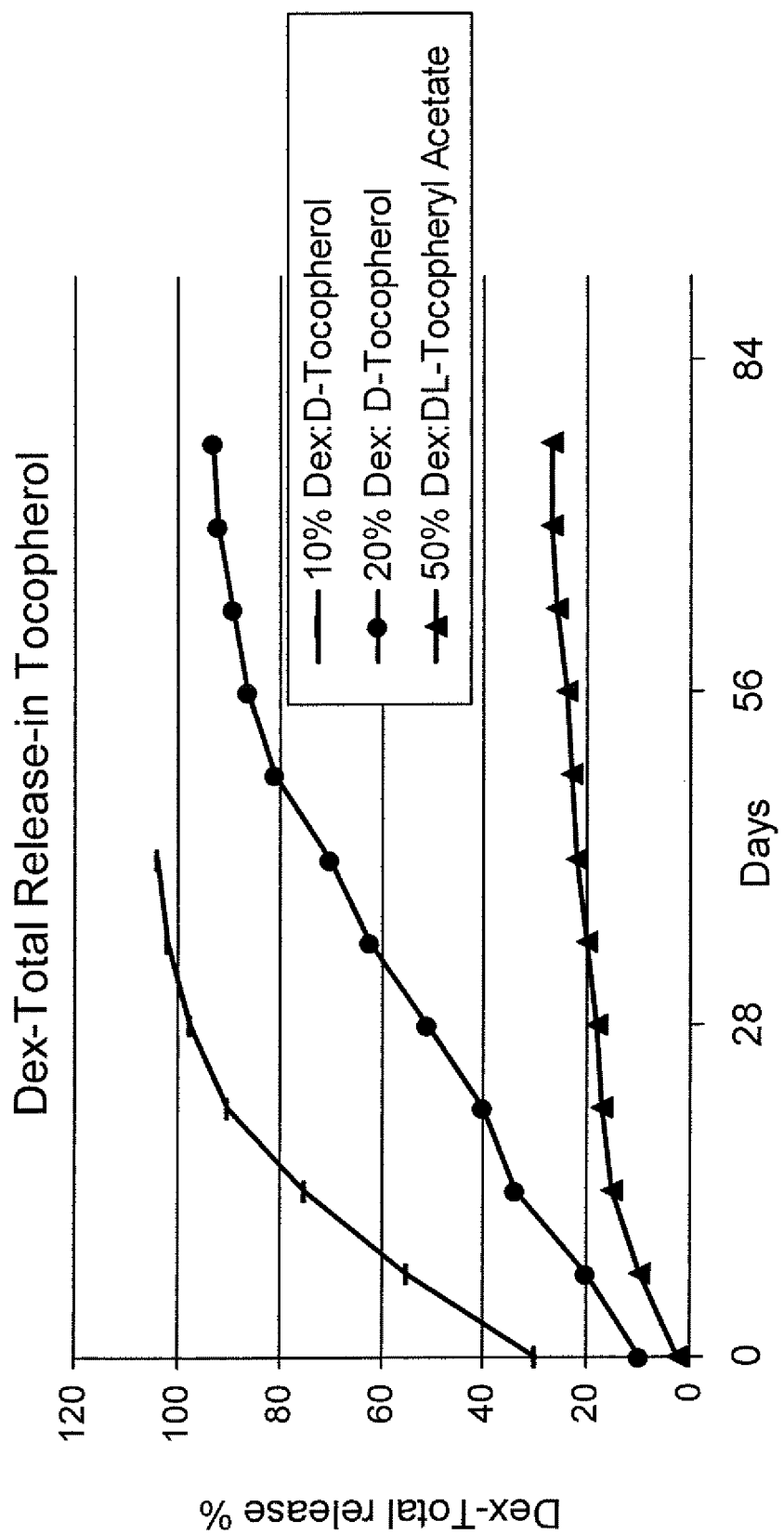
FIG. 1 depicts dissolution profiles of dexamethasone (Dex) released from three formulations of Dex/d-tocopherol, and dl-tocopheryl acetate.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to an excipient is a reference to one or more such excipients, including equivalents thereof known to those skilled in the art. Other than in the operating examples, or where otherwise indicated, all numbers expressing quantities of ingredients or reaction conditions used herein should be understood as modified in all instances by the term "about."

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

Unless defined otherwise, all technical and scientific terms used herein have the same meaning as those commonly understood to one of ordinary skill in the art to which this invention pertains.

The present invention relates to novel biocompatible, biodegradable sustained release topical formulations suitable for administration to the eye. In various aspects of the invention these formulations are liquids, gels, ointments, or emulsified micells (oil in water or water in oil). The formulations include at least one active agent which is delivered in a limited solubility, biocompatible, biodegradable (often referred to herein as LSBB) formulation. The LSBB formulations of the present invention deliver therapeutic and non-toxic levels of active agents over the desired extended time frame. These formulations are both biocompatible and biodegradable, and disappear harmlessly after delivering active agent.

The present invention provides for sustained release eye drop formulations for topical administrations of beneficial, active agents to the eye. Topical eye drops are directed generally to therapies for the anterior segments of the eye, which are the contemplated therapies for the formulations of this invention, The anterior segment includes the anterior chamber, iris, ciliary body, lens, and the eye surface. The eye surface is composed of the cornea, conjunctiva, eye lids, lacrimal and meibomian glands, and the interconnecting nerves. The tocopherols and their esters of low water solubility, notably α-tocopheryl acetate, are exceptional vehicles for biocompatible, nonirritating topical eye drop formulations providing sustained release of beneficial agents for periods of at least about four days from a single application without interfering with vision.

Specific areas of the human or animal body to be targeted for topical applications of the excipient/active agents LSBB compositions include, but are not limited to: eyes, punctum lacrimale (tear ducts), nasal passages, mucosa of the nasal cavity and throat, The formulations according to the present invention have particular applicability in providing a controlled and sustained release of active agents effective in obtaining a desired local or systemic physiological or pharmacological effect relating at least to the treatment of eye infections, or modification of the immune response, such as preventing and treating transplant rejection, and providing therapy for chronic dry eye syndrome.

More specifically, the LSBB formulations are useful for treating ocular conditions such as glaucoma, PVR, diabetic retinopathy, uveitis, retinal edema, vein occulusion, macular degeneration. Irvine-Gass Syndrome and CMV retinitis, corneal diseases such as keratitis, and corneal transplantation rejection by mediating homograft rejection with formulations comprising sirolimus or cyclosporine. The formulations may also be prepared as control-release eye drops for dry-eye or for controlling the immune response. Regarding control of immune responses, the formulations may contain one or more of cyclosporine, sirolimus, or tacrolimus. Other intraocular uses include glaucoma treatments (e.g., formulations including timolol or prostaglandins such as latanoprost), antibiotic delivery, antibody delivery, and antiproliferatives delivery (e.g., paclitaxel).

Additional maladies of the ocular tissues that may be treated with the formulations of the present invention include eye lid indications such as hordeolum, chalazaion, rosacea, blepharitis, squamous, and basal carcimona. Corneal indications include corneal infections, dry eye, Fuchs' dystrophy, herpes zoster (shingles), iridocorneal endothelial syndrome, keratoconus, lattice dystrophy, map-dot-fingerprint dystrophy, herpes simplex, pterygium, Stevens-Johnson Syndrome, acute or chronic focal immunological corneal graft reaction or rejection and following any corneal transplant procedures. Diseases of the lacrimal glands include allergic, inflammatory, infectious, traumatic, malignant, and autoimmune diseases. Conjunctival indications include conjunctivitis (pink eye, allergic, bacterial, viral, giant papillary, keratoconjunctivits, inclusion), neoplasms (dermoid cysts, squamous cell carcinoma of the conjunctiva, papilloma, acquired melanosis of the conjunctiva, malignant melanoma of the conjunctiva, nevus of the conjunctiva, vascular tumors), pterygium and pinguecula, xerophalmia, subconjuctival hemorrhage, dry-eye syndrome, and Sjögren's syndrome. Glaucoma indications are open-angle glaucoma and narrow angle glaucoma and neovascular glaucoma. Diseases of the iris include albinism, aniridia, coloboma, iritis, melanoma, metastases and Waardenburg syndrome, and epithelial cysts. Surgical indications are any post-surgical inflammatory and infection induced by Lasik corneal procedures, cataract extraction, glaucoma surgery, conjunctival and/or mucous membrane transplantation. Other ocular maladies to be considered include exophthalmos, scleritis, episcleritis, Grave's disease, pseudotumor of the orbit, lymphoma of the orbit, tumors of the orbit, orbital cellulitis, pre-phthisical ocular hypotomy, neovascular glaucoma, and anterior uveitis of inflammatory or infectious etiology.

Further regarding corneal indications, an aspect of the invention provides for a formulation for limiting tissue rejection following corneal transplant. Corneal transplant, also known as a corneal graft or penetrating keratoplasty, involves the removal of the central portion (called a 'button') of the diseased cornea and replacing it with a matched donor button of cornea. Corneal grafts are performed on patients whose damaged or scarred corneas (a result of disease or trauma), prevent acceptable vision. Formulations of the present invention useful in corneal transplant contexts may include rapamycin, cyclosporin, or a combination of these active agents.

Some common types of beneficial agents administered by topical eye drops for treatment of the maladies of the eye and contemplated for the formulations of the present invention include β-blockers, prostaglandin analogs, α2-adrenergic agonists, miotic agents, sympathomimetics, carbonic anhydrase inhibitors, antibiotics, steroidal anti-inflammatories, NSAIDs, antihistamines, immunsuppressive agents, and lubricants.

Further regarding glaucoma or increased intraocular pressure, medication classes historically used in the management of glaucoma include beta blockers, miotics, sympathomimetics and carbonic anhydrase inhibitors. Because topically applied medications are more site-specific, they are preferred in the treatment of glaucoma. Compared with oral medications, topical agents are associated with a decreased incidence of systemic side effects. With current topical formulations, conjunctival and localized skin allergic reactions are fairly common, whereas severe reactions, including death, are rare. Recently introduced topical agents for glaucoma therapy include dorzolamide and brinzolamide, the first topical carbonic anhydrase inhibitors; brimonidine and apraclonidine, more ocular-specific alpha agonists; and latanoprost, a prostaglandin analog, which is a new class of glaucoma medication. Like their predecessors, the newer agents lower intraocular pressure by a statistically significant degree. Preservation of visual field, the more substantial patient-oriented end point, continues to be studied. An example formulation of the present invention, particularly useful for lowering intraocular pressure, consists of α tocopheryl acetate and the prostaglandin, latanoprost. In vivo, eye drops consisting of prostaglandin and tocopheryl acetate, applied once weekly, maintained low intraocular pressure in rabbit eyes for at least three months.

A wide variety of other disease states are known by those of ordinary skill in the art, such as those described in Goodman & Gilman, THE PHARMACOLOGICAL BASIS OF THERAPEUTICS (McGraw Hill, 2001), and REMINGTON'S PHARMACEUTICAL SCIENCES (Lippincott Williams & Wilkins; 20th ed., 2000). Those to which the present invention may be applied may be determined by those with ordinary skill in the art without undue experimentation.

Suitable classes of active agents for use in the system of the present invention include, but are not limited to: Peptides and proteins such as cyclosporin, insulins, glucagon-like-peptides, growth hormones, insulin related growth factor, botulinum toxins (Botox, Allergan), antibodies, and heat shock proteins; Anesthetics and pain killing agents such as lidocaine and related compounds, and benzodiazepam and related compounds; Anti-cancer agents such as 5-fluorouracil, methotrexate and related compounds; Anti-inflammatory agents such as 6-mannose phosphate; Anti-fungal agents such as fluconazole and related compounds; Antiviral agents such as trisodium phosphomonoformate, trifluorothymidine, acyclovir, cidofovir, ganciclovir, ddI, and AZT; Cell transport/mobility impeding agents such as colchicines, vincristine, cytochalasin B, and related compounds; Anti-glaucoma drugs such as beta-blockers: timolol, betaxolol, and atenolol; Immunological response modifiers such as muramyl dipeptide and related compounds; Steroidal compounds such as dexamethasone, prednisolone, triamcinolone and related compounds; and Carbonic anhydrase inhibitors such as acetazolamide, brinzolamide, dorzolamide, and timolol maleate.

In addition to the above agents, other active agents which are suitable for administration, especially to the eye and its surrounding tissues, to produce a local or a systemic physiologic or pharmacologic effect can be used in the system of the present invention. Examples of such agents include antibiotics such as tetracycline, chloramphenicol, ciprofloxacin, ampicillin, and the like.

The present formulations provide for the use of formulations comprising excipients characterized as of limited solubility, biocompatible, and biodegradable (LSBB), for controlled and sustained release of an active agent or a combination of active agents. Liquid or gel controlled-sustained release systems can be fabricated by combining an LSBB excipient and an active agent. Formulations may include more than one biodegradable component as well as more than one active agent. Gels can be produced by vortex or mechanical mixing. Liquid formulations can be made by pre-mixing in a suitable container, or mixing of the excipient and the active agent before or at the time of administration. A typical method of mixing an excipient and active agent uses sonication.

As noted, the excipient of the present invention is biodegradable or bioerodible. As used herein, the terms "bioerodible" and "biodegradable" are equivalent and are used interchangeably. Biodegradable excipients are those which degrade in vivo, and wherein erosion of the excipient over time is required to achieve the agent release kinetics according to the invention.

The excipient is also biocompatible, meaning that it does not have undue toxicity or cause either physiologically or pharmacologically harmful effects. In the context of topical formulations for the eye, it should be understood that some initial "stinging" or minor discomfort is common with eye drops, but such minor reactions do not render the present formulations non-biocompatible.

In an aspect of the present invention, the novel biocompatible and biodegradable liquid and gel formulations, which may be conveniently topically placed on the human or animal eye for the sustained release of active agent(s), are obtained by admixing one or more excipients, such as, for example: d, l and dl isomers of α, β, δ, ε, η tocopherols and similar isomers of the tocotrienols and the esters of these tocopherols and tocotrienols with straight and branched chain C2 to C20 aliphatic acids, or their esters of C3 to C20 straight chain dicarboxylic acids; the mono, di, and tri esters of O-acetylcitric acid or O-propionylcitric acid or O-butyrylcitric acid with C1 to C10 straight and branched chain aliphatic alcohols; the mono, di, and tri esters of citric acid with C1 to C10 straight and branched chain aliphatic alcohols; and omega-3 fatty acids or esters thereof; with a large number of established and new active agents.

In another aspect of the invention, the gel formulations generally contain about 20% to about 80% of an LSBB excipient, and liquid formulations generally contain about 30% to about 99.9% of an LSBB excipient. These proportions depend on the nature (e.g., solubility) of the particular active agent and the particular LSBB excipient. It should be noted that the active agent and the LSBB excipient provides the sustained release of the active agent, rather than additional excipients (e.g., coatings) or delivery vehicles (e.g., structures).

Examples of excipients that may be useful as biocompatible, biodegradable and/or bioerodible excipients in the present invention, as determined by one of ordinary skill in the art in light of this specification, without undue experimentation, include, but are not limited to d-α-tocopherol; d,l-α-tocopherol; d-β-tocopherol; d,l-β-tocopherol; d-η-tocopherol; and d,l-η-tocopherol (including acetate); tocotrienol isomers, and their esters, tocotrienol isomers; the mono, di, and tri esters of O-acetylcitric acid or O-propionylcitric acid or O-butyrylcitric acid with C1 to C10 straight and branched chain aliphatic alcohols, the mono, di, and tri esters of citric acid with C1 to C10 straight and branched chain aliphatic alcohols; and omega three fatty acids and their esters.

Further regarding tocopherols, this biodegradable/biocompatible excipient useful in the present invention refers to the family of tocopherols and tocotrienols and derivatives thereof. Tocopherols and tocotrienols are derivatives of the simplest tocopherol, 6-hydroxy-2-methyl-2-phytylchroman. Tocopherols are also known as a family of natural or synthetic compounds commonly called Vitamin E. Alpha-tocopherol is the most abundant and active form of this class of compounds. Other members of this class include β-, γ-, and δ-tocopherols and α-tocopherol derivatives such as tocopheryl acetate, succinate, nicotinate, and linoleate, but the latter derivatives may have limited solubility that renders them unsuitable for some formulations. Useful tocotrienols include d-δ-tocotreinols, and d-β-, d-γ-tocotrienols, and their esters. In particular, the tocopherols and their esters of low water solubility, notably α-tocopheryl acetate, are exceptional vehicles for biocompatible nonirritating topical eye drop formulations that provide sustained release of pharmaceutical agents for periods up to one week from a single application, without interfering with vision.

In another aspect of the invention, a low solubility active agent may be combined with a biodegradable, biocompatible excipient of higher solubility to result in a LSBB formulation. For example, dimethyl sulfone may be used as a binder in a LSBB formulation of a limited solubility active agent. Hence, the use of a soluble excipient in a LSBB formulation is within the scope of the present invention.

In yet another aspect of the invention, a surfactant may also be included in the formulation, particularly when the active agent is in an aqueous solution or state. For example, TPGS is a pharmaceutically approved surfactant constructed from lipophilic α tocopherol attached to hydrophilic PEG 1000 through a succinate linkage. TPGS may be used in tocopherol formulations (such as dl-α tocopheryl acetate) in which the aqueous component exceeds about 0.5% (wt). For example, a stable mixture of saline and α tocopheryl actetate (EA) may be prepared (for example, by sonication) in ratios ranging from about 1:2 to 1:4 (saline:EA). Similarly, water and EA may be prepared in stable formulations at ratios ranging from about 1:2 to 1:4 ($H_2O$:EA) with TPGS added at about 2.5% as an emulsifier. These emulsions are stable, and suitable for aqueous-based active agents.

Any pharmaceutically acceptable form of the active agents of the present invention may be employed in the practice of the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate, and the like.

The active agents may also be used in combination with pharmaceutically acceptable carriers in additional ingredients such as antioxidants, stabilizing agents, and diffusion enhancers. For example, where water uptake by the active agent is undesired, the active agent can be formulated in a hydrophobic carrier, such as a wax or an oil, that would allow sufficient diffusion of the active agent from the system. Such carriers are well known in the art.

Examples of proteins and proteinaceous compounds which may be formulated and employed in the delivery system according to the present invention include those proteins which have biological activity or which may be used to treat a disease or other pathological condition. They include, but are not limited to antibodies, growth hormone, Factor VIII, Factor IX and other coagulation factors, chymotrypsin, trysinogen, alpha-interferon, beta-galactosidase, lactate dehydrogenase, growth factors, clotting factors, enzymes, immune response stimulators, cytokines, lymphokines, interferons, immunoglobulins, retroviruses, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and geserelin, LHRH agonists and antagonists, growth hormone releasing factor, callcitonin, colchicines, gonadotropins such as chorionic gonadotropin, oxytocin, octreotide, somatotropin plus and amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagons, and endocrine agents secreted internally and distributed by way of the bloodstream.

Other agents, such as $\alpha_1$ antitrypsin, insulin, glucagon-like-peptides, and other peptide hormones, botulinum toxins (Botox®, Allergan, Inc.), adrenal cortical stimulating hormone, thyroid stimulating hormone, and other pituitary hormones, interferons such as α, β, and δ interferon, erythropoietin, growth factors such as GCSFm GM-CSF, insulin-like growth factor 1, tissue plasminogen activator, CF4, dDAVP, tumor necrosis factor receptor, pancreatic enzymes, lactase, interleukin-1 receptor antagonist, interleukin-2, tumor suppresser proteins, cytotoxic proteins, viruses, viral proteins, recombinant antibodies, portions of antibodies, and antibody fragments and the like may be used. Analogs, derivatives, antagonists, agonists, and pharmaceutically acceptable salts of the above may also be used.

The protein compounds useful in the formulations of the present invention can be used in the form of a salt, preferably a pharmaceutically acceptable salt. Useful salts are known to those skilled in the art and include salts with inorganic acids, organic acids, inorganic bases, or organic bases.

Other active agents encompassed in the present invention include prodrugs. Because prodrugs are known to enhance numerous desirable qualities of pharmaceuticals (e.g., solubility, bioavailability, manufacturing, etc.) the pharmaceutical dosage forms of the present invention may contain compounds in prodrug form. Thus, the present invention is intended to cover prodrugs of the presently claimed active agents, methods of delivering the same, and compositions containing the same.

Analogs, such as a compound that comprises a chemically modified form of a specific compound or class thereof, and that maintains the pharmaceutical and/or pharmacological activities characteristic of said compound or class, are also encompassed in the present invention. Similarly, derivatives such as a chemically modified compound wherein the modification is considered routine by the ordinary skilled chemist, such as an ester or an amide of an acid, protecting groups, such as a benzyl group for an alcohol or thiol, and tert-butoxycarbonyl group Active agents, or active ingredients, or beneficial agents, that may be useful in the present invention singly or in combination, as determined by one of ordinary skill in the art in light of this specification without undue experimentation, include but are not limited to the following agents and the pharmaceutically acceptable salts thereof:

Angiostatic and/or Anti-inflammatory Steroids such as anecortive acetate (Retaane®, Alcon, Inc., Fort Worth, Tex.); tetrahydrocortisol; 4,9(11)-pregnadien-17α,21-diol-3,20-dione (Anecortave) and its -21-acetate salt; 11-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its 21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide (Diamox®, Lederle Parenterals, Inc., Carolina, Puerto Rico; several other manufacturers);

Anti-neovascularization Steroids such as 21-nor-5β-pregnan-3α,17α,20-triol-3-acetate; 21-nor-5α-pregnan-3α,17α,20-triol-3-phosphate; 21-nor-5β-pregn-17(20)en-3α,16-diol; 21-nor-5β-pregnan-3α,17β,20-triol; 20-acetamide-21-nor-5α-pregnan-3α,17α-diol-3-acetate; 3β acetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-one-21-methyl ether; 20-azido-21-nor-5β-pregnan-3α,17α-diol; 20(carbethoxymethyl)thio-21-nor-5β-pregnan-3α,17α-diol; 20-(4-fluorophenyl)thio-21-nor-5β-pregnan-3α, 17α-diol; 16α-(2-hydroxyethyl)-17β-methyl-5β-androstan-3α, 17αdiol; 20-cyano-21-nor-5β-pregnan-3α,17α-diol; 17α-methyl-5β-androstan-3α,17β-diol; 21-nor-5β-pregn-17(20)en-3α-ol; 21-or-5β-pregn-17(20)en-3α-ol-3-acetate; 21-nor-5-pregn-17(20)-en-3α-ol-16-acetic acid 3-acetate; 3β-azido-5β-pregnan-11β,17α,21-triol-20-one-21-acetate; and 5β-pregnan-11β,17α,21-triol-20-one; 4-androsten-3-one-17β-carboxylic acid; 17α-ethynyl-5(10)-estren-17β-ol-3-one; and 17α-ethynyl-1,3,5(10)-estratrien-3,17β-diol;

Nonsteroidal Anti-inflammatories such as naproxin; diclofenac; celecoxib (Celebrex®, Pfizer); sulindac; diflunisal; piroxicam; indomethacin; etodolac; meloxicam; ibuprofen; ketoprofen; r-flurbiprofen (Myriad Genetics, Inc.); mefenamic; nabumetone; tolmetin, and sodium salts of each of the foregoing; ketorolac bromethamine; ketorolac tromethamine (Acular®, Allergan, Inc.); choline magnesium trisalicylate; rofecoxib; valdecoxib; lumiracoxib; etoricoxib; aspirin; salicylic acid and its sodium salt; salicylate esters of α,β,γ-tocopherols and tocotrienols (and all their d, l, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; and phenylbutazone;

Angiogenesis Inhibitors such as squalamine, squalamine lactate (Evizon™, Genaear Corp.) and curcumin; Vascular endothelial growth factor (VEGF) inhibitors including pegaptanib (Macugen®, Eyetech/Pfizer), bevacizumab (Avastin®, Genentech, Inc.), concentrated shark cartilage extract (Neovastat®, Eterna Zentaris), PTK 787 (vatalanib, Schering AG/Novartis), ribozyme anti-angiogenic (Angiozyme®, Sirma Therapeutics, Inc./Chiron Corp.); AZD 6474 (Zactima®, AstraZeneca AB Ltd.), anti-angiogenesis chimeric monoclonal antibody specific VEGF receptor 2 (IMC-1C11, ImClone Sys. Inc.), isocoumarin 2-(8-hydroxy-6-methoxy-1-oxo-1H-2-benzopyran-3-yl) propionic acid (NM-3, Ilex Oncology Inc,), SU668 (Pfizer), isopropoxymethyl-12-(3-hydroxypropyl) ideno[2,1-a]pyrro[3,4-c]carbazole-5-one (CEP-5214, Cephalon), CEP-7055 (the N,N-dimethyl glycine ester prodrug of CEP-5214, Cephalon), and PTC299 (PTC Therapeutics); Integrin antagonists such as anti-α$_v$β$_3$ antibody (Vitaxin®, Medimmune Inc.); RDG peptide mimetics such as S137 and S247 (Pfizer), conformationally constrained bicyclic lactam Arg-Gly-Asp-containing pseudopeptides such as ST1646 (Sigma Tau S.p.A.); DPC A803350 (Bristol-Myers Squibb), and o-guanidines (3D Pharmaceuticals Inc.); matrix metalloproteinase inhibitors such as prinomastat (AG 3340, Pfizer), (ISV-616, InSite Vision), (TIMP-3, NIH); S3304 (Shionogi); BMS 275291 (Celltech/Bristol-Myers Squibb); SC 77964 (Pfizer); ranibizumab (Lucentis®, Genentech, Inc.); ABT 518 (Abbott Labs.); CV 247 (Ivy Medical); NX-278-L anti-VEGF aptamer (EyeTech Pharm.); 2'-O-mrthoxyethyl antisense C-raf oncogene inhibitor (ISIS-13650, Isis Pharm., Inc./iCo Therapeuticals, Inc.); vitronectin and osteopontin antagonists (3D Pharm.); combretastatin A-4 phosphate (CA4P, OxiGene, Inc.); fab fragment α-V/β-1 integrin antagonist (Eos-200-F, Protein Design Labs); α-v/β-3 integrin antagonist (Abbott Labs.); urokinase plasminogen activator fragment (A6, Angstrom Pharm.); VEGF antagonists (including AAV-PEDF, Chiron Corp.; VEGF-R, Johnson & Johnson/Celltech; SU10944, Sugen/Pfizer; VEGF-TRAP, Regeneron; SP-(V5.2)C, Supratek Pharm. Inc.; endostatin VEGF antagonist, EntreMed, Inc. (Rockville, Md.); kdr tyrosine kinase inhibitor (EG-3306, Ark Therapeutics); cytochalasin E (NIH); kallikrinin-binding protein (Medical Univ, SC); combretastatin analog (MV-5-40, Tulane); pigment-epithelium derived growth factor (Med. Univ. SC); AdPEDF, GenVec, Inc.); plasminogen kringle (Medical Univ. SC); rapamycin; cytokine synthesis inhibitor/p38 mitogen-activated protein kinase inhibitor (SB-220025, GlaxoSmithKline); FGF1 receptor antagonist/tyrosine kinase inhibitor (Pfizer/Sugen); bradykinin B1 receptor antagonist (B-9858, Cortech, Inc.); bactericidal/permeability-increasing protein (Neuprex®, Xoma Ltd.); protein kinase C inhibitor (Hypericin, Sigma-Aldrich, St. Louis, Mo.); ruboxistaurinn mesylate (LY-333531, Eli Lilly & Co.); polysulphonic acid derivatives (Fuji Photo Film); growth factor antagonists such as TBC-2653 and TBC-3685 (Texas Biotech. Corp.); Tunica internal endothelial cell kinase (Amgen Inc.);

Anti-bacterials including aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; rifampin; dapsone; atovaquone; rifabutin; linezolide; polymyxin B and its hydrochloride, sulfate, or phosphate salt; sulfacetamide and its sodium salt; minocycline; and clarithromycin;

Anti-infective Agents such as 2,4-diaminopyrimidines (e.g., brodimoprim, tetroxoprim, trimethoprim); nitrofurans (e.g., furaltadone, furazolium chloride, nifuradene, nifuratel, nifurfoline, nifurpirinol, nifurprazine, nifurtoinol, nitrofuirantoin); quinolones and analogs (e.g., cinoxacin, ciprofloxacin, clinafloxacin, difloxacin, enoxacin, fleroxacin, flumequine, gatifloxacin, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin); sulfonamides (e.g., acetyl sulfamethoxypyrazine, benzylsulfamide, chloramine-b, chloramine-t, dichloramine t, $n^2$-formylsulfisomidine, $n^4$-β-d-glucosylsulfanilamide, mafenide, 4'-(methylsulfamoyl) sulfanilanilide, noprylsulfamide, phthalylsulfacetaride, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole); sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone); and others (e.g., clofoctol, hexedine, methenamine, methenamine anhydromethylene-citrate, methenamine hippurate, methenamine mandelate, methenamine sulfosalicylate, nitroxoline, taurolidine, and xibomol); moxifloxacin; and gatifloxacin;

Antivirals such as amprenavir; interferon alfa-n3; interferon alfa-2b; interferon alfacon-1; peginterferon alfa-2b; interferon alfa-2a; lamivudine; zidovudine; amadine (Symmetrel®, Endo Pharm. Inc.) and its hydrochloride, sulfate, and phosphate salts, indinavir and its hydrochloride, sulfate, or phosphate salt; ganciclovir; ganciclovir sodium salt; famciclovir; rimantadine and its hydrochloride, sulfate, or phosphate salt; saquinavir mesylate; foscarnet; zalcitabine; ritonavir; ribavirin; zanamivir; delavirdine mesylate; efavirenz; amantadine and its hydrochloride, sulfate, or phosphate salt; palivizumab; oseltamivir and its hydrochloride, sulfate, or phosphate salt; abacavir and its hydrochloride, sulfate, or phosphate salt; valganciclovir and its hydrochloride, sulfate, or phosphate salt; valacyclovir and its hydrochloride, sulfate, or phosphate salt; didanosine; nelfinavir mesylate; nevirapine; cidofovir; acyclovir; trifluridine; penciclovir; zinc oxide; zinc salicylate; zinc salts of all isomers of tocopherol hemisuccnic acid; zinc salts of straight, branched, saturated, and unsaturated chain $C_2$ to $C_{20}$ aliphatic carboxylic acids; zinc pyruvate; zinc lactate; zinc ester complexes; and zinc acetoacetonate or zinc acetoacetic ester complexes;

Insulins such as Novolog® (insulin aspart [rDNA origin]) and Novolin® products (Novo Nordisk Inc.); Humalog® (insulin lispro [rDNA origin]), Humalog® 75/25 and 50/50 (mixtures of insulin lispro protamine suspension and insulin lispro), and Humulin® products (regular human insulin [rDNA origin], Eli Lilly & Co.); Lantus® (insulin glargine [rDNA origin], Sanofi Aventis U.S. LLC); porcine and bovine insulins;

Glucagon-like Peptide-1 (Glp1) and analogs (for diabetes therapy and appetite suppression, cardiac protection) (see Keiffer et al., 20 Endocr Rev., 876-913 (1999) such as liraglutide (Novo Nordisk Inc.); Glp1 receptor stimulators such as such as Byetta® products (exenatide, and incretin mimetic, Amylin Pharm., Inc./Eli Lilly & Co.) and ZP-10 (Zealand Pharma A/S); Glp-1-albumin (ConjuChem Inc.); and Dpp-IV inhibitors (which inhibit enzyme attack on Glp-1) such as Galvus® (vildagliptin, formerly LAF237, Novartis), Januvia® sitagliptin, formerly MK-0431, Merck & Co.); saxagliptin (formerly BMS-477188, Bristol-Myers Squibb), and GSK23A (GlaxoSmithKline);

Alpha Androgenergic Agonist such as brimonidine tartrate;

Beta Adrenergic Blocking Agents (Beta blockers) such as betaxolol (Betoptic®, Betoptic® S betaxolol hydrochloride suspension, Alcon Labs., Inc.), and its hydrochloride, sulfate, or phosphate salt; levobetaxolol and its hydrochloride, sulfate, or phosphate salt; and timolol maleate (Timoptic®, Timoptic-XE®, timolol maleate ophthalmic gel-forming solution, Merck & Co.), levobunolol (Betagan®, levobunolol hydrochloride ophthalmic solution, Allergan), carteolol (Ocupress®, carteolol hydrochloride ophthalmic solution, CIBA Vision Sterile Mfg./Novartis Ophthalmics), metipranolol (OptiPranolol®, metipranolol ophthalmic solution, Bausch & Lomb);

Carbonic Anhydrase Inhibitors such as brinzolamide (Azopt®, brinzolamide hydrochloride, Alcon Labs., Inc.), dorzolamide (Trusopt®, dorzolamide hydrochloride, Merck & Co.), and its drochloride, sulfate, or phosphate salt; and dichlorphenamide (Merck);

Sympathomimtics such as epinephrine-like dipivefrin (Propine®, dipivefrin hydrochloride, Allergan), and clonodine-like bimonidine (Alphagan®, brimonidine tartrate, Allergan) and apraclonidine (Iopidine®, aprapclonidine hydrochloride, Alcon);

Mast Cell Stabilizers such as pemirolast (Alamast® pemirolast potassium ophthalmic solution, Vistakon Pharma., LLC), and its potassium salt; nedocromil ophthalmic (Alocril®, Allergan, Inc.) and its sodium salt; cromolyn and its sodium salt (PendoPharm);

Mioties (Cholinesterase Inhibitors) such as demecarium bromide, pilocarpine (Isopto Carpine, Ocusert Pilo);

Prostaglandins and prostaglandin alalogs such as bimatoprost (Lumigan® bimatoprost ophthalmic solution, Allergan); travoprost (Travatan® travoprost ophthalmic solution, Alcon Inc.); and latanoprost (Xalatan® latanaprost ophthalmic solution, Pfizer);

Antihistamines such as olopatadine and its hydrochloride, sulfate, or phosphate salt forms; fexofenadine and its hydrochloride, sulfate, or phosphate salt; azelastine and its hydrochloride, sulfate, or phosphate forms; diphenhydramine and its hydrochloride, sulfate, or phosphate forms; and promethazine and its hydrochloride, sulfate, or phosphate forms;

Antimicrotubule Agents such as Taxoids including paclitaxel (Taxol®, Bristol-Myers Squibb); vincristine (Oncovin®, Eli Lilly & Co.) and its hydrochloride, sulfate, or phosphate salt forms; vinblastine (Velbe®, Eli Lilly & Co.) and its hydrochloride, sulfate, or phosphate salt; vinorelbine (Navelbine®, Fabre Pharm. Inc.); colchicines; docetaxel (Taxotere®, Sanofi-Aventis U. S. LLC); RPR-109881 (Sanofi-Aventis); LIT 976 (Sanofi-Aventis); BMS 188797 and BMS 184476 (Bristol-Myers Squibb); DJ 927 (Daiichi Pharm. Inc.); DHA-paclitaxel (Taxoprexin®, Protarga, Inc.); Epothilones including epothiloneB such as patupilone (EPO 906, Novartis/generic), BMS 247550 and BMS-310705 (Bristol-Myers Squibb), epothilone D (KOS 862, Kosan Biosci. Inc.), and ZK EPO (Schering AG);

Antineoplastic agents such as doxorubicin and its hydrochloride, sulfate, or phosphate salt; idarubicin and its hydrochloride, sulfate, or phosphate salt; daunorubicin and its hydrochloride, sulfate, or phosphate salt: dactinomycin; epirubicin and its hydrochloride, sulfate, or phosphate salt; dacarbazine; plicamycin; mitoxantrone (Novantrone®, EMD Serono Inc.) and its hydrochloride, sulfate, or phosphate salt; valrubicin; cytarabine; nilutamide; bicalutamide; flutamide; anastrozole; exemestane; toremifene; femara; tamoxifen and tamoxifen citrate; temozolomide (Temador, Schering-Plough Corp.); gemcitabine and its hydrochloride, sulfate, or phosphate salt; topotecan and its hydrochloride, sulfate, or phosphate salt; vincristine and its hydrochloride, sulfate, or phosphate salt; liposomal vincristine (Teva Pharm.); methotrexate and methotrexate sodium salt; cyclophosphamide; estramustine sodium phosphate; leuprolide and leuprolide acetate: goserelin and goserelin acetate; estradiol; ethinyl estradiol; Menest® esterified estrogens (Monarch Pharm., Inc.); 5-flurouracil; bortezamib (Velcade®, Millennium Pharm., Inc.);

Antiapoptotics such as desmethyldeprenyl (DES, RetinaPharma Tech., Inc., Philadelphia, Pa.);

Aldose Reductase Inhibitors such as GP-1447 (Grelan); NZ-314 (parabanic acid derivative, Nippon Zoki); SG-210 (Mitsubishi Pharm/Senju); and SJA-7059 (Senju);

Antihypertensives such as candesartan cilexetil (Atacand®, Takeda Pharm. Co./AstraZeneca AB); losartan (Cozaar® and Hyzaar®, Merck & Co.); and lisinopril (Zestril®, AstraZeneca AB and Prinivil®, Merck & Co.);

Antioxidants such as benfotiamine (Albert Einstein College Med./WorWag Pharma); ascorbic acid and its esters; tocopherol isomers and their esters; and raxofelast (IRFI 016, metabolized to IRFI 005, Biomedica Foscama);

Vitrectomy Agents such as hyaluronidase (Vitrase®, ISTA Pharm., Inc.);

Adenosine Receptor Antagonist such as A2B adenosine receptor antagonist (ATL-754, Adenosine Therapeutics, LLC);

Adenosine Deaminase Inhibitor such as pentostatin (Nipent®, SuperGen Inc.);

Glycosylation Antagonists such as pyridoxamine (Pyridorin™, NephroGenex Inc.);

Topoisomerase Inhibitors such as doxorubicin (Adriamycin®, Pfizer; Caelyx™ Schering-Plough Pharm.; Doxil®, Johnson & Johnson/Pharmacia/generics); daunorubicin (DaunoXome®, Gilead Sci.); etoposide (Vepesid® and Etopophos®, Bristol-Myers Squibb); idarubicin (Idamycin PFS®, Pfizer); irinotecan (Camptosar®), Pfizer); topotecan (Hycamtin®, GlaxoSmithKline); epirubicin (Ellence®, Pfizer); and raltitrexed (Tomudex®, AstraZeneca);

Anti-metabolites such as methotrexate (generic) and its sodium salt; 5-fluorouracil (Adrucil®, Teva Pharm. U.S.); cytarabine (Cytosar®, Upjohn Co.); fludarabine (Fludara®, Bayer HealthCare Pharm.) and its forms as salts with acids; gemcitabine (Gemzar®, Eli Lilly & Co.); capecitabine (Xeloda®, Roche Labs. Inc.); and perillyl alcohol (POH, Endorex);

Therapeutic Antibodies including Herceptin® (trastuzumab, Genentech. Inc.). MDX-H210 (Medarex, Inc.); SGN-15 (Seattle Genetics); H11 (Viventia); Therex (Antisoma); rituximan (Rituxan®, Genentech); Campath (ILEX Oncology/Millennium/Shering); Mylotarg (Celltech/Wyeth); Zevalin (IDEC Pharmaceuticals/Schering); tositumomab (Bexxar®, GlaxoSmithKline); epratuzumab (Lymphocide, Immunomedics/Amgen); Oncolym® (Techniclone Corp./ Schering AG); Mab Hu1D10 antibody (Protein Design Laboratories); ABX-EGF (Abigenix); infleximab (Remicade®, Centocor) and etanercept (Enbrel®, Wyeth-Ayerst);

Tyrosine Kinase Inhibitors/Epidermal Growth Factor Receptor Inhibitors such as gefitinib (Iressa, AstraZeneca, ZD 1839); trastuzumab (Herceptin®, Genentech); erlotinib (Tarceva, OSI Pharmaceuticals, OSI 774); cetuximab (Erbitux, Imclone Systems, IMC 225); and pertuzumab (Omnitarg, Genentech, 2C4);

Cytotoxins such as Irofulven (MGI 114, MGI Pharma);

Neurotensin Antagonist such as SR 48692 (Sanofi-Synthelabo);

Peripheral Sigma Ligands such as SR 31747 (Sanofi-Synthelabo);

Endothelin ETA/Receptor Antagonists such as YM-598 (Yamanouchi); and atrasentan (ABT-627, Abbott);

Anti-glaucoma Agents such as prostaglandins: latanoprost, bimaloprost, travoprost; dorzolamide (Cosopt™ dorzolamide hydrochloride hydrochloride-timolol maleate ophthalmic solution, Merck); β blockers: timolol (acid-free and amine salts forms), levobunolol, betaxolol (Kerlone® beta-adrenergic blocking agent, Sanofi-Aventis), and its hydrochloride, sulfate, phosphate salts; atenolol; a 2-adrenergic antagonists: brimonidine; sympathmimetics: epinephrine, dipivetrin; miotic agents: philicarpine; carbonic anhydrase inhibitors; dorzolamide, brinzolamide, acetolamide; and chlorthalidone (PLIVA®, Inc., East hanover, N.J.);

Immunsuppressive Agents such as sirolimus (rapamycin, Rapamune®, Wyeth-Ayerst); tacrolimus (FK506) (Prograf®, Astella Pharma US, Inc.); and cyclosporins;

Nucleic acids such as small interfering NAs (siRNA) or KA interference (RNAi), particularly, for example siRNAs that interfere with VEGF expression; antisense oligonucleotides such as Affinitac (Isis Pharma./Eli Lilly & Co.); and Genasence (Genta/Aventis);

Additional active agents include triamcinolone-16,21-diacetate; triamcinolone acetonide; fluocinolone acetonide; dexamethasone; dexamethasone-21-acetate; dexamethasone-21-(3,3-dimethylbutyrate); dexamethasone-21-phosphate disodium salt; dexamethasone-21-diethylaminoacetate; dexamethasone-21-isonicotinate; dexamethasone -21-dipropionate; dexamethasone-21-palmitate; betamethasone; betamethasone-21-acetate; betamethasone-21-adamantoate; betamethasone-17-benzoate; betamethasone-17,21-dipropionate; betamethasone-17-valerate; betamethasone-21-phosphate disodium salt; naproxen; diclofenac; celecoxib; rofecoxib; valdecoxib; etoricocib; lumiracoxib; pegaptanib octasodium; 2-methoxyestradiol; combretstatin A-4 phosphate (CA4P, Oxigene); urokinase plasminogen activator fragment (A6, Angstrom Pharm.); bradykinin B1 receptor antagonist (B-9858, Cortech); acetylcysteine; mannitol; antineoplaston; human corticotropin-releasing factor; VN40101M (Pediatric Brain Tumor Consortium) everolimus; GW572016 (NCI); thalidomide; temozolomide; tariquidar; doxorubicin; dalteparin; tarceva; CC-5013 (NCI); hCRF (Xerecept® corticorelin acetate injection, Neurobiological Tech., Inc., Emeryville, Calif.); melphalan; thiotepa; depsipeptide; erlotinib; tamoxifen; bortezomib; lenalidomide; vorinostat; temsirolimus; modifinil; enzastuarin; motexafin gadolinium; F-18-OMFD-PET (Advanced Biochem. Compounds, Redeberg); pemetrexed disodium; ZD6474 (NCI); valproic acid; vincristine; irinotecan; PEG-interferon alpha-2b; procarbazine; lonafarnib; arsenic trioxide; GP96 (Univ. Cal., San Francisco, Calif.); carboplatin; cyclophosphamide; 1311-TM-601 (Trans Molecular); lapatinib; O6-benzylguanine; TP-38 toxin (NCI); cilengitide; poly-ICLC (NCI); FR901228 (NCI); TransMid™ (Xenova); talabostat; ixabepilone; AEE788 (Jonson Comprehensive Cancer Center); alanosine; sorafenib; efaproxiral; carmustine; iodine I 131 monoclonal antibody TNT-1/B (NCI, Bethesda, Md.); intratumoral TransMid™; topatecan; lomustine; phosphorus 32; 18F-fluorodeoxyglucose (Alberta Cancer Board); vinblastine; BMS-247550 (NCI); CC-8490 (NCI); IL 13-PE38QQR (Neopharm); imatib mesylate; hydroxyurea; G207 (MediGene); radiolabeled monoclonal antibody; 2-deoxyglucose; talampanel; retinoic acid; gefitinib; tipifarnib; CPT-11 (Kentuckiana Cancer Inst); rituximab; efaproxiral; PS-341 (FDA Office Orphan Prod. Devel.); capecitabine; G-CFS (NCI); vinorelbine; paclitaxel; patipilone (Norvatis); iressa; methotrexate; ABT-751 (NCI); oxaliplatin; MS-275 (NCI); trastuzumab; pertuzumab; PS-341 (NCI); 17AAG (NCI); lenalidomide; campath-1H; somatostatin analog; resveratrol; CEP-7055 (Cephalon); CEP-5214 (Cephalon); PTC-299 (PTC Therapeutics); inhibitors of hepatocyte growth factor (L2G7mAb, Galaxy Biotech); statins such as atorvastatin (Lipitor®, Pfizer), fluvastatin (Lescor®, Novartis), rosuvastatin (Crestor®, Astra Zeneca), prevastatin (Provacol®, Teva Pharm.), simvastatin (Zocar®, Merck & Co., Inc.), lovastatin (Mevorcor®, Merck), or cervastatin (Baycol®, Bayer AG) (HMG-CoA reductase inhibitors); and Receptor tyrosine kinase inhibitors.

Those of ordinary skill in the art will appreciate that any of the foregoing disclosed active agents may be used in combination or mixture in the pharmaceutical formulations of the present invention. Such mixtures or combinations may be delivered in a single formulation, or may be embodied as different formulations delivered either simultaneously or a distinct time points to affect the desired therapeutic outcome. Additionally, many of the foregoing agents may have more than one activity or have more than one therapeutic use, hence the particular category to which they have been ascribed herein is not limiting in any way. Similarly, various biodegradable, biocompatible excipients may be used in combination or in mixtures in single or multiple formulations as required for a particular indication. These mixtures and combinations of active agents and excipients may be determined without undue experimentation by those of ordinary skill in the art in light of this disclosure.

The formulations of the present invention may be sterilized for use by methods known to those of ordinary skill in the art. Autoclaving and e-beam have been used in informal studies of several embodiments and have not appeared to have significant impact. Similarly, informal stability studies indicate acceptable stability of several embodiments. Additionally, reproducibility between aliquots and lots is very good, with a standard deviation of less than five percent or better. Hence, standard pharmaceutical manufacturing techniques are readily applied to the technologies described herein.

An example embodiment of the present invention comprises the active agent dexamethasone and the excipient tocoperol. Dexamethasone is a glucocorticoid and typically used in the form of the acetate or disodium phosphate ester. Glucocorticoids are adrenocortical steroids suppressing the inflammatory response to a variety of agents that can be of mechanical, chemical or immunological nature. Doses vary depending on the condition treated and on the individual patient response. In ophthalmology, dexamethasone sodium phosphate (Decadron®, Merck & Co.) as a 0.1% solution has been widely used since its introduction in 1957. The ophthalmic dose depends on the condition treated, but for control of anterior chamber inflammation the topical dose is usually around 0.5 mg per day.

For treatment following cataract surgery, or for other treatments or diseases of the eye, an aspect of the invention provides for a composition comprising an active agent and the LSBB excipient useful for the treatment of iris neovascularization from cataract surgery, macular edema in central retinal vein occlusion, cellular transplantation (as in retinal pigment cell transplantation), cystiod macular edema, psaudophakic cystoid macular edema, diabetic macular edema, pre-phthisical ocular hypotomy, proliferative vitreoretinopathy, proliferative diabetic retinopathy, exudative age-related macular degeneration, extensive exudative retinal detachment (Coat's disease), diabetic retinal edema, diffuse diabetic macular edema, ischemic ophthalmopathy, chronic focal immunalogic corneal graft reaction, neovascular glaucoma, pars plana vitrectomy (for proliferative diabetic retinopathy), pars plana vitrectomy for proliferatve vitreoretinopathy, sympathetic ophthalmia, intermediate uveitis, chronic uveitis, intraocular infection such as endophthalmitis, and/or Irvine-Gass syndrome.

Another embodiment of the invention provides formulations and uses of the tocopherols and/or tocotrienols and their esters with insulins for the delivery of the insulins in the management of diabetes. Tocopherols and/or the tocotrienols and their esters possess outstanding capabilities to carry therapeutic agents, especially moderate molecular weight proteins such as the insulins, through the mucosa and membrane surfaces of the eye area, or through the nasolacrimal drainage system, into the body. Pillion et al., 32 Invest. Ophthalmol. & Visual Sci. 3021-27 (1991). Indeed, it is contemplated that wide variety of other therapeutic agents (such as steroids, NSAIDs, antibiotics, hormones, growth factors, anti-cancer agents, etc.) may be available for effective delivery formulations with the tocopherols and/or tocotrienols and their esters via eye drops.

The present invention relates generally to the use of compounds that are liquid, of limited solubility, biocompatible and biodegradable for controlled and sustained release of an agent or a combination of an agents. Gel or liquid controlled-sustained release systems can be fabricated by combining an excipient discussed herein and an active agent. Systems can combine more than one of these excipients as well as more than one beneficial agent. Gels can be produced by vortex or mechanical mixing. Liquid formulations can be made by pre-mixing in an appropriate container or mixing of the excipient and the beneficial agent at the time of administration Another aspect of the present invention provides for embodiments comprising omega-3 fatty acids. The health benefits of dietary supplements of omega-3 fatty acids and their esters are well known. The particularly important omega-3 fatty acids in human nutrition are α-linolenic acid (ALA, C18H30O2, fw 278.4) eicosapentaenioc acid (EPA, C20H30O2, fw 306.5) and docosahexaenoic acid (DHA, C22H32O2, fw 328.5). The term omega-3 signifies that the first double bond exists between the third and second carbon atoms counting from the terminal methyl at the opposite end of the chain from the carbonyl group.

The human body cannot synthesize EPA or DHA except by using ALA as an intermediate. But the presence of EPA and DHA in almost all tissues of the body indicates the importance of these compounds to the body and thus the judicious injection into the body of their therapeutic formulations will be safe, efficient and effective. These benefits also extend to the simple esters of EPA and DHA of the $C_1$ to $C_8$ straight and branched chain aliphatic alcohols such as ethyl EPA and ethyl DHA. Recently, the FDA has approved ethyl EPA and ethyl DHA for dietary supplements. One important property of these ethyl esters is that they can be fractionally distilled from their readily available but crude source, fish oil. This purification process provides the EPA and DHA esters free from possible heavy metal and PCB contaminants. Thus, there remains a need for the development of these purified esters as liquid excipient vehicles for injectable sustained drug release in various areas of the human or animal body.

The embodiments thus provide for the novel concept of injections of omega-3 fatty acids and their esters by themselves or as novel and therapeutic formulations with active agents directly into strategic areas of the human or animal bodies to provide for the sustained release of the omega-3 compounds and therapeutic but nontoxic levels of the active agents for periods of months to over a year.

Yet another embodiment of the present invention relates generally to novel topically applied formulations containing both steroids and antioxidants. Specifically, the inclusion of antioxidants with steroids addresses the problem that many steroids have harmful side effects arising from their being initiators of destructive oxidative and photo-oxidative radical chain reactions. These novel steroid-antioxidant formulations are designed to be applied topically, externally for the known steroid therapies of anti-inflammation and regulation of metabolic and immune functions, but also due to the presence of antioxidants to suppress damaging oxidative free radical reactions initiated by the steroids in addition to harmful oxidative chemistries normally present in cells.

Although oxygen is required for many life sustaining metabolic reactions, it also has damaging chemistries with cellular components, involving very reactive oxygen components: superoxide radicals, hydrogen peroxide, hydroxyl radicals, and organic peroxides and hydroperoxides. Polyunsaturated lipids are important components of cells, but they are major substrates for oxidative attack leading to cell death. Thus, the dependence of cells on oxygen places them a precarious position between the prolife and toxic chemistries of oxygen.

Cells contain protective antioxidant molecules such as tocopherol, ascorbic acid, glutathione, melatonin, carotenes, carnitine, and others. The natural level of tocopherol in the human lens is around 2.2 μg/ml (Yeum et al., 19(6) Curr. Eye Res. 502-05 (1999)), and the ascorbate level in tears is 3.52 μg/ml (Choy et al., 80(9) Optom. Vis. Sci. 632-36 (2003)). Unfortunately the exposure of cells to some steroids, even though for very necessary therapeutic reasons, has been found to tip this balance towards the toxic side. It has been demonstrated that these steroids, especially the glucocorticosteroids such as triamcinolone and dexamethasone, readily interact with oxygen and/or light to become initiators of damaging oxidative chain reactions. Miolo et al. 78(5) Photochem. & Photobiol., 425-30 (2003); Calza et al., 12(12) J. Am. Soc. Mass. Spectrom., 1286-95 (2001). Although the co-administration of certain antioxidants with certain steroids has been shown to ameliorate the toxic oxidative processes initiated by the steroids (Kosano et al., 76(6) Exp. Eye Res., 643-48 (2001)), most commercially available injectable steroid formulations do not include antioxidants. See Fact sheet inserts for Kenalog™, Bristol-Myers Squibb, 2006; Depo Medrol™, Pharmacia, 2003; Decadron™, Merck Sharp & Dohme, 1995, (contains bisulfites, hydroxybenzoate esters which might have antioxidant effects). In formulating compositions containing antioxidant supplements one must be very careful not to add too high a level of antioxidants, however, because it has been demonstrated that at high levels many of these antioxidants actually are pro-oxidants and may increase oxidative damage. Bowry et al., 270 J. Biol. Chem. 5756-63 (1995); Halliwell, 25 Free Rad. Res. 439-54 (1996). Using the naturally occurring antioxidants and mimicking their levels in the cell environment would be good practice, The steroid components and excipients of these novel formulations and their therapeutic effects are well described herein and in U.S. Patent Application Publication No. 2008/0038316. The possible adverse effects of the steroids used in these formulations are in many cases believed to arise from the aforementioned damaging oxidative chemistries initiated by these steroids in the absence of proper antioxidants. The environment of the eye is particularly damaging for it is exposed to both oxygen and light energy. The phenolic or quinone-like structures of the steroid molecules readily absorb UV-A and UV-B radiation to convert these molecules to unpaired electron radical species. These radical species can damage cell components (especially unsaturated lipids in cell membranes) or they can interact with oxygen to instigate damaging peroxy chain reactions leading to cataracts (Nishigori et al., 35(9) Life Sci. 981-85 (1984); Boscia et al., 41(9) Invest. Ophthalmol. Vis. Sci. 2461-65 (2000)), and glaucoma (Sacca et al. 84(3) Exp. Eye Res. 389-99 (2007)). Cataract formation and glaucoma are maladies associated with steroid therapies in the eye. In the case of intra-articular steroid therapies repeated injections are avoided because they lead to cartilage and bone degeneration. Reactive oxygen species have been identified as causative agents. Kim et al., 49(9) Free Radic. Biol. Med. 1483-93 (2006).

In the context of the present formulation in which the LSBB excipient/active agent formulation provides for the sustained release of the active agent, other components may be added to the formulation as are known in the art of eye drops or topical formulations. Additionally, the formulations of the present invention may be combined with other therapies or interventions following standard acceptable best practices.

Without further elaboration, one skilled in the art having the benefit of the preceding description can utilize the present invention to the fullest extent. The following examples are illustrative only and do not limit the remainder of the disclosure in any way.

EXAMPLES

Example 1

The Assay Procedure for Measuring the Release Profiles of Dexamethasone or Triamcinolone Acetonide from Sustained Release Formulations

The vials for the release studies were labeled and the weight of each vial was recorded. To each vial was added 3 grams-4 grams of 0.9% saline solution and the weight was recorded. Then the formulation was injected or placed at the bottom of the vial, The weight of the formulation was recorded. An additional amount of 0.9% saline solution was added to a total of 10 grams of saline. The resulting vial was kept in an incubator or water bath at 37° C. Samples were taken periodically to measure the release profile of dexamethasone or triarmcinolone acetonide using a HPLC instrument. Sampling protocol was carried out according to the following procedure: Using a disposable pipette, 8 grams of the saline solution containing dexamethasone or triamcinolone acetonide was withdrawn carefully from each vial. Eight (8) grams of 0.9% saline solution was then added to each vial. The vials were kept at 37° C. after sampling.

The HPLC analysis was carried out using a Beckman Gold Instrument with an autosampler. Calibrators with three different concentrations of dexamethasone or triamcinolone acetonide in water were prepared. Calibrators and samples were injected onto a C18 column (Rainin, 250×4.6 mm) containing a guard column (C18, 4.6 mm×1 cm) and analyzed, respectively. The column was eluted using a mobile phase of 45% (or 50%) acetonitrile/water, flow rate 1.0 ml/min, and 7 min or 6 min run time at an ambient temperature. The detector wavelength of 238 nm was used. The dexamethasone or triamcinolone acetonide (retention times, 6 min-4 min) concentration of each sample was calculated from the standard curve using the software of the Beckman Gold instrument.

A wash program to clean the HPLC column was set up during the HPLC run. After every three or four injections, a sample containing 20 µl of acetonitrile was injected onto the column, the column was eluted with a mobile phase of 99% acetonitrile/water, flow rate 1 ml/min, and a run time 7 min. Then the column was equilibrated back to the original mobile phase by injecting 20 µl of acetonitrile, eluting with 45% (or 50%) acetonitrile/water, flow rate I ml/min, and a run time 7 min.

The sampling times and the active ingredient (for example dexamethasone or triamcinolone acetonide) concentrations determined from HPLC were recorded and tabulated. The percent drug released and the amount of drug released were each calculated from a Microsoft Excel software program.

Example 2

Preparation of Mixtures of Dexamethasone in a Tocopherol and Their Release Profiles

For the preparation of 10% dexamethasone (Dex) in d-tocopherol, one portion by weight of Dex was mixed with nine portions by weight of d-tocopherol. The resulting suspension was stirred at an ambient temperature until a homologous mixture formed. The mixture was then aliquoted and analyzed for release profile as shown in FIG. 1.

For the preparation of 20% Dex in d-tocopherol, two portions by weight of Dex was mixed with eight portions by weight of d-tocopherol. The resulting suspension was stirred at an ambient temperature until the formation of a homologous mixture. The mixture was then aliquoted and analyzed for release profile as shown in FIG. 1.

For the preparation of 50% Dex in dl-tocopheryl acetate, five portions by weight of Dex were mixed with five portions by weight of dl-tocopheryl acetate. The resulting suspension was stirred at ambient temperature until a homologous mixture formed. The mixture was then aliquoted and analyzed for the release profile as shown in FIG. 1.

Example 3

Omega-3 Fatty Acids and Their Esters for Liquid Sustained Drug Release Formulations

The embodiments provide for the novel concept of formulations of omega-3 fatty acids and their esters by themselves or as novel and therapeutic formulations with active agents directly into strategic areas of the human or animal bodies to provide for the sustained release of the omega-3 compounds and therapeutic but nontoxic levels of the active agents for periods of months to over a year.

The process of applying small amounts of these omega-3 fatty acid/ester alone or their formulations containing active agents at the site of the malady is not only maximally effective and efficient but also avoids the waste and potentially increased danger of systemic oral administration. These novel sustained drug release formulations of the omega-3 liquids alone or in combination with the other excipients disclosed herein and in U.S. Patent Application Publication No. 2008/0038316 can be applied topically to the eye. Among a number of maladies to be treated, as listed herein and in U.S. No. 2008/0038316, are those of the retina such as macular degeneration, retinitis pigmentosa, proliferative vitreoretinopathy, to name a few. A potentially advantageous property of DHA, EPA, and their esters is their importance in maintaining healthy retinal tissue and their required presence for proper development of neonatal retinal function. See, e.g., Jeffrey et al., 36(9) Lipids 859-71 (2001); SanGiovanni & Chew, 24(1) Prog Retin Eye Res. 87-138 (2005); Bazan, 29(5) Trends Neurosci. 263-71 (2006); King et al., 26(17) J. Neurosci. 4672-80 (2006).

Some more specific, but not limiting, examples contemplated for ocular therapies are for inflammatory maladies of the eye. Topical administration may include, for example, 10 µl to 60 µl liquid microspheres of ethyl DHA/ethyl EPA alone or as mixtures containing 10% to 50% by weight of microcrystalline dexamethasone or triamcinolone acetonide. This provides for the maintenance of therapeutic levels of the omega-3 fatty acids or the therapeutic concentration of the steroids in the area of the eye for extended periods. In the case of anti-VEGF therapy similar amounts of such agents as ranibizumab or bevacizumab could be employed in a similar manner with the omega-3 excipients. The extensive list of other beneficial agents employed for the list of a wide variety of maladies are disclosed herein and in U.S. No. 2008/0038316.

Example 4

Formulations Containing Steroids and Antioxidants

This embodiment relates generally to novel topically applied formulations containing both steroids and antioxidants. These formulations allow the application of steroids to achieve their intended benefits (anti-inflammation, immune modulation) without initiation of harmful oxidative chemistries, These example formulations are composed of one or more of the steroids listed in Group A combined with one or more of the antioxidants listed in Group B and all dispersed or dissolved in one or more of the delivery vehicles selected from the excipients described herein and listed in Group C and also described in U.S. No. 2008/0038316.

| Group A Steroids | |
|---|---|
| triamcinolone | dexamethasone diethyl aminoacetate |
| triamcinolone acetonide | dexamethasone isonicotinate |
| triamcinolone diacetate | dexamethasone palmitate |
| triamcinolone acetate | prednisone |
| triamcinolone disodium phosphate | prednisolone |
| triamcinolone hemisuccinate | prednisolone acetate |
| triamcinolone benetonide | prednisolone sodium phosphate |
| dexamethasone | methylprednisolone |
| dexamethasone acetate | methylprednisolone acetate |
| dexamethasone | methylprednisolone |
| disodium phosphate | sodium succinate |
| dexamethasone 3,3- | paramethasone |
| dimethylbutyrate | etrahydrocortexolone |
| cortisone | betamethasone |
| cortisone acetate | betamethasone acetate |
| hydrocortisone | betamethasone disodium |
| hydrocortisone acetate | phosphate |
| tetrahydrocortisol | betamethasone benzoate |
| fludrocortisones | betamethasone valerate |
| fludrocortisone acetate | betamethasone dipropionate |
| fludrocortisone phosphate | betamethasone adamantoate |
| anacortive | beclomethasone |
| anacortive acetate | beclomethasone dipropionate |
| mometasone furoate | diflorasone |
| fluocinolone | diflorasone diacetate |

| Group B Antioxidants | |
|---|---|
| ascorbic acids and salts | retinyl palmitate |
| ascorbyl palmitate | probucol |
| ascorbyl dipalmitate | erythorbic acid |
| ascorbyl stearate | sodium erythorbate |
| ascorbyl-2,6-dibutyrate | α-lipoic acid |
| d-tocopherol (α,β,γ,δ isomers) | isocitrate |
| dl-tocopherol | lutein/zeaxanthin/ |
| (α,β,γ,δ isomers) | meso-zeaxanthin |
| the acetate, hemisuccinate, nicotinate | eugenol |
| and succinate-PEG ester derivatives of | isoeugenol |
| the above tocopherol isomers | (−)-epicatechin |
| glutathione | (−)-epigallocatechin gallate |
| β-carotine | benzyl alcohol |
| carnitine | benzyl benzoate |
| carnitine | 2,6-di-tertbutyl-4- |
| acetate | methoxy phenol |
| trans reveratrol | butylated hydroxytoluene |
| retinoic acid | butylated hydroxyanisole |
| retinyl palmitate | quercetin |
| melatonin | catechin |
| timolol | rutin |
| luteolin | coenzyme Q |
| kaempferol | fisetin |
| thyroxine | methyl gallate |
| pyrroloquinolone | superoxide dismutase |

| Group C Exipients | |
|---|---|
| d-tocopherol (α,β,γ,δ isomers) | |
| dl-tocopherol (α,β,γ,δ isomers) | |
| the acetate and esters of C-3 to C-10 | |

| Group C Exipients | |
|---|---|
| straight and branched chain aliphatic acids with the above tocopherol isomers | |
| dimethyl sulfone (MSM) | omega-3 fatty acids and their ester with C-1 to C-10 straight and branched chain aliphatic alcohols |
| triethyl, tripropyl, or tribuyl esters of O-acetyl, O-propionyl, or O-butyryl citrate | tri-straight and branched chain C-1 to C-10 aliphatic alcohol esters of citric acid |

As mentioned above, to avoid harmful pro-oxidative chemistries care should be taken not to expose the cells to too high a level of the antioxidants. This may present a problem as formulators develop a one-shot formulation that administers steroids and antioxidants for months to a year or more. The formulation must incorporate enough antioxidants to last this long without releasing pro-oxidative concentrations. This is achieved in this embodiment of the invention by using lipophyllic prodrug forms of the antioxidants such as ascorbyl palmitate, tocopheryl acetate, benzyl benzoate, and the like, which slowly release the active, more hydrophyllic form into the cellular environment upon hydrolysis.

Examples of a sustained release formulation of this embodiment include formulations such as:

| (1) | α-tocopheryl acetate | 60 pts/wt |
|---|---|---|
|  | ascorbyl palmitate | 10 pts/wt |
|  | triamcinolone acetonate | 40 pts/wt |
| (2) | α-tocopheryl acetate | 60 pts/wt |
|  | ascorbyl palmitate | 10 pts/wt |
|  | dexamethasone | 40 pts/wt |

Example 6

Sustained Release Eye Drop Formulation Containing Cyclosporin

Figure 2:
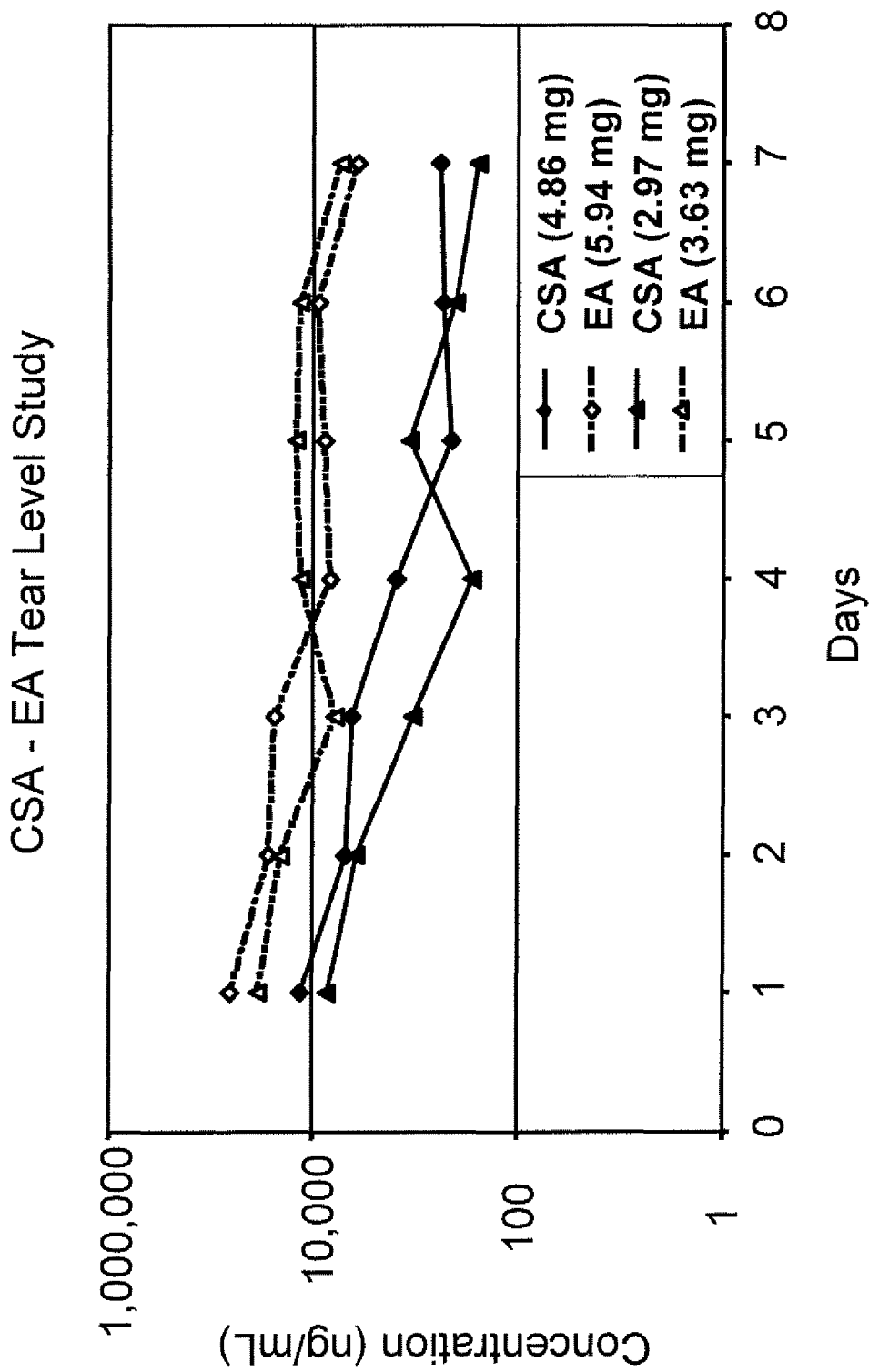
FIG. 2 shows cyclosporin A (CSA) release in rabbit tears following installation of one drop of a 45:55 (wt) CSA:α-tocopheryl acetate (EA) formulation.
Figure 3:
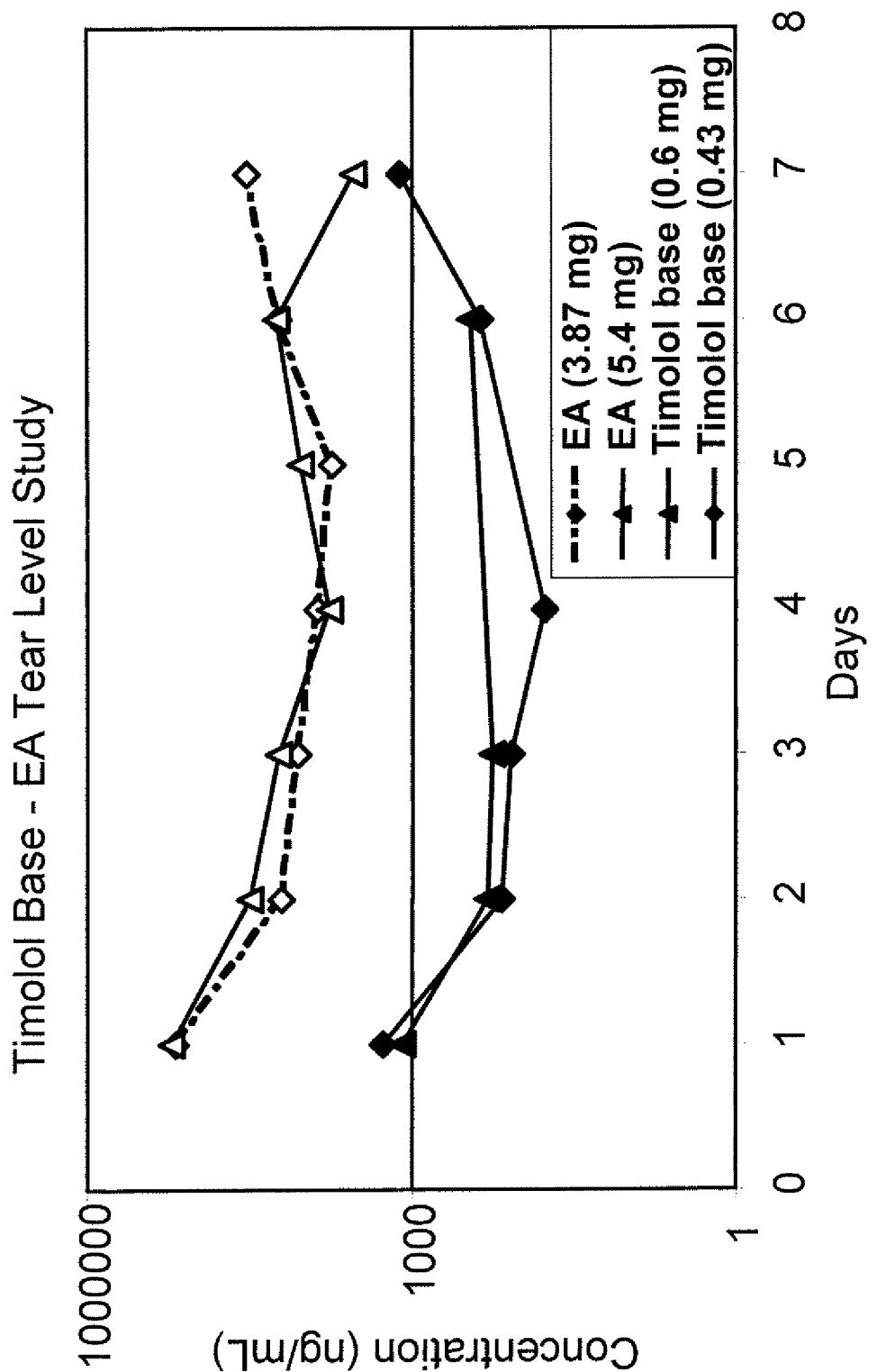
FIG. 3 shows timolol release in rabbit tears following installation of one drop of a 10:90 (wt) timolol:dl-tocopheryl acetate (EA) formulation.

Instillation of droplets of about 10 mg of α-tocopheryl acete (ATA) onto the front of the eyes of human volunteers revealed that there was no irritation and the liquid quickly spread around the periphery of the anterior surface leaving vision unblurred. Inspection showed that the ATA, probably because of its low water solubility, remained in the eye for periods exceeding seven days. Subsequently, as shown in FIG. 2 and FIG. 3, formulations of ATA:cyclosporin A (Chemwerth, Woodbrigdge, Conn.) or ATA:timolol were instilled into rabbit eyes to reveal that therapeutic levels of these active agents were continuously released to the tears for periods of seven days. No indications of irritation were observed.

Regarding FIG. 2, a (45:55) by wt formulation of cyclosporin A (CSA) in ATA was instilled topically as one eye drop onto one eye of two NZW 4.0 kg rabbits. Droplet weighing 6.6 mg (▲) and 10.8 mg (♦) were instilled. Tear samples were collected daily by filter paper, weighed, eluted in 300 μl MeOH, and analysed for CSA and ATA by LCMSMS.

Regarding FIG. 3, a (10:90) by wt formulation of timolol base (Sifavitor, Italy) in dl-α-tocopheryl acetate was instilled topically as eye one drop onto one eye of two NZW 4.0 kg rabbits. Droplets weighing 4.3 mg (♦) and 6.0 mg (▲) were instilled. Tear samples were collected daily by filter paper, weighed, eluted in 300 μl MeOH, and analysed for timolol base and tocopheryl acetate by LCMSMS.

Example 7

Sustained Release Eye Drop Formulation Containing Dexamethasone

Eye drop formulations included 10% or 20% dexamethasone in d-tocopherol were prepared as follows: One portion by weight of dexamethasone was mixed with nine portions by weight of d-tocopherol. The resulting suspension was stirred at an ambient temperature until there was a formation of a homogeneous mixture. The mixture was then aliquoted and analyzed for release profile. Two portions by weight of dexamethasone were mixed with eight portions by weight of d-tocopherol. The resulting suspension was stirred at an ambient temperature until there was a formation of a homogeneous mixture. The mixture was then aliquoted and analyzed for release profile. For 50% dexamethasone in dl-tocopheryl acetate, five portions by weight of dexamethasone were mixed with five portions by weight of dl-tocopheryl acetate. The resulting suspension was stirred at an ambient temperature until there was a formation of a homogeneous mixture. The mixture was then aliquoted and analyzed for release profile, as shown in FIG. 4, It is contemplated that novel, non-irritating, long-lasting sustained drug release topical eye drop formulations comprise a tocopherol or omega-3 fatty acid selected from Group A, combined with at least one of the active agents listed in Group B.

Group A Excipients; $\alpha$, $\beta$, $\gamma$, $\delta$ tocopherols; $\alpha$, $\beta$, $\gamma$, $\delta$ tocotrienols; the esters of tocopherol and tocotrienols isomers with C1 to C10 straight and branched chain aliphatic carboxylic acids (such as acetates) d, l, and dl isomers of the tocopherols, tocotrienols and their esters, for example $\alpha$ tocopheryl acetate; the mono, di, and tri esters of O-acetylcitric acid or O-propionylcitric acid or O-butyrylcitric acid with C1 to C10 straight and branched chain aliphatic alcohols; the mono, di, and tri esters of citric acid with C1 to C10 straight and branched chain aliphatic alcohols; and omega-3 fatty acids.

Group B Beneficial Agents, as discussed in many of the preceeding paragraphs; anti-glaucoma agents; immunsuppressive agents; angiostatic and/or anti-inflammatory steroids; nonsteroidal anti-inflammatories; anti-infective agents; anti-bacterials; antivirals; $\alpha$ androgenergic agonists; $\beta$ adrenergic blocking agents; mast cell stabilizers; antihistamines; antimicrotubule agents; antineoplastic agents; topoisomerase inhibitors: anti-metabolites; and antibody therapeutic agents.

Example 8

Tocopherol/Latanoprost Eye Drops Intraocular Pressure in the Rabbit Eye

Duplicate experiments were run in two NZW rabbits. Intraocular pressures (IOPs) were measured using Tono-Pen® tonometer (Reichert, Inc.). Each eye of each rabbit was monitored for five days without treatment to establish baseline values. At day 5, one drop of approximately 50 μl drops of 0.005% latanoprost in α tocopheryl acetate (EA) was placed into one eye of each rabbit. The other eye received a drop of 0.9% NaCl in water. IOPs were monitored for another ten days.

Figure 5A:
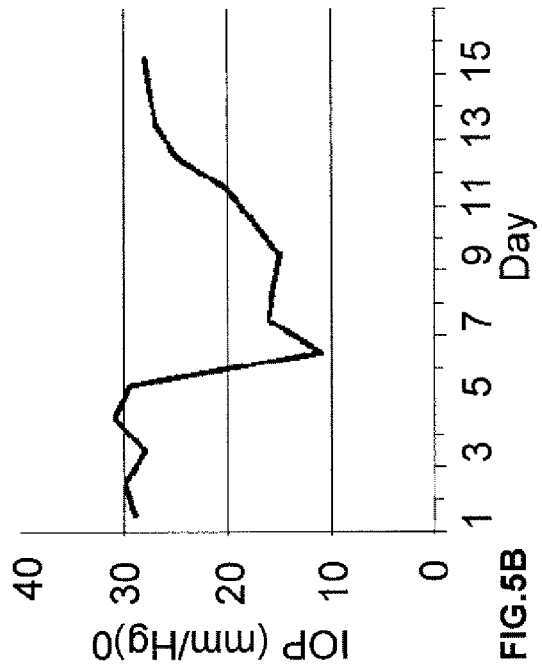
FIGS. 5A-5D are charts showing the intraocular pressure of two rabbits treated with a saline in one eye; and a formulation of latanaprost in dl-tocopheryl acetate in the other eye.
Figure 5B:
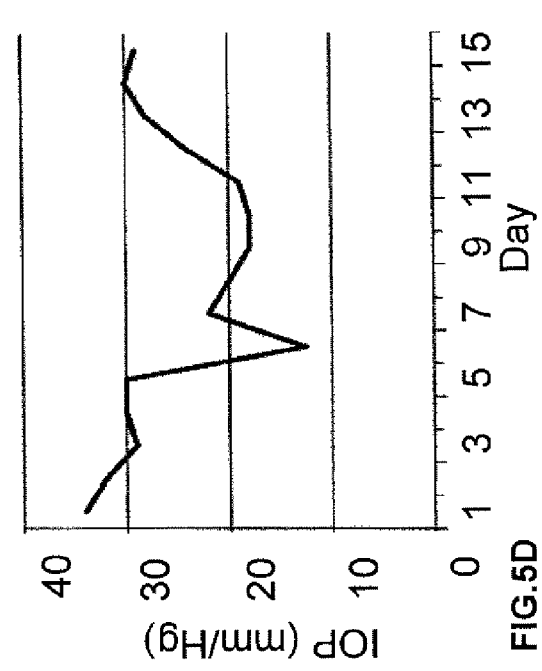
Figure 5C:
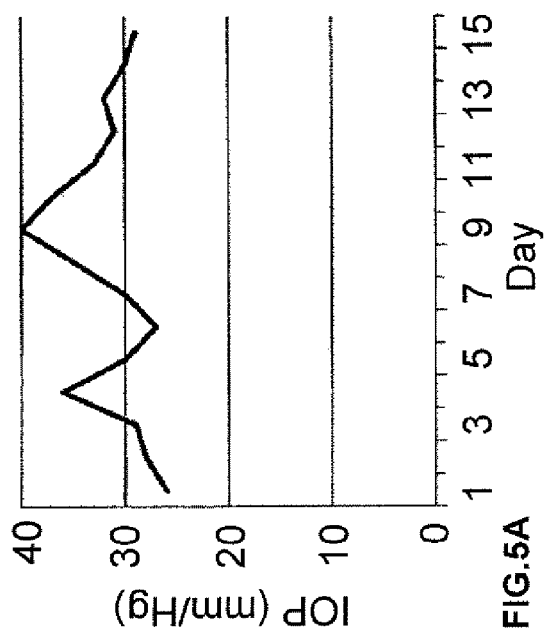
Figure 5D:
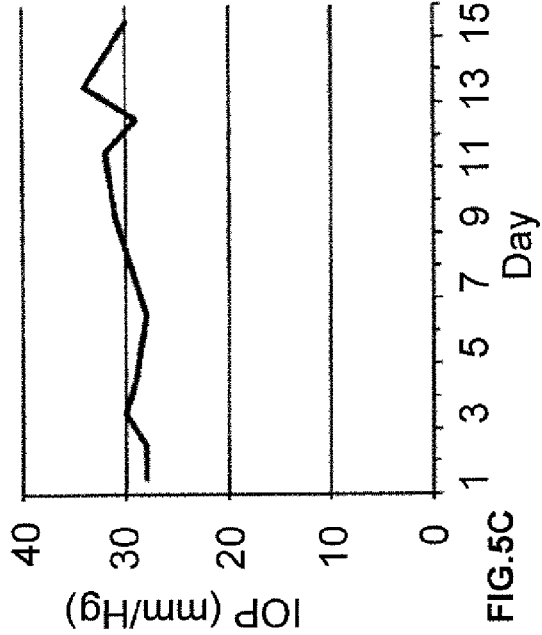

As shown in FIGS. 5B and 5D, the eyes treated with one drop of the latanoprost/EA formulation exhibited a decrease in IOP that was sustained over several days as compared to the saline-treated eyes (FIGS. 5A and 5C).

Example 9

In vitro Study of Dexamethasone in Triethyl O-Acetyl Citrate (TEAC)

Figure 6:
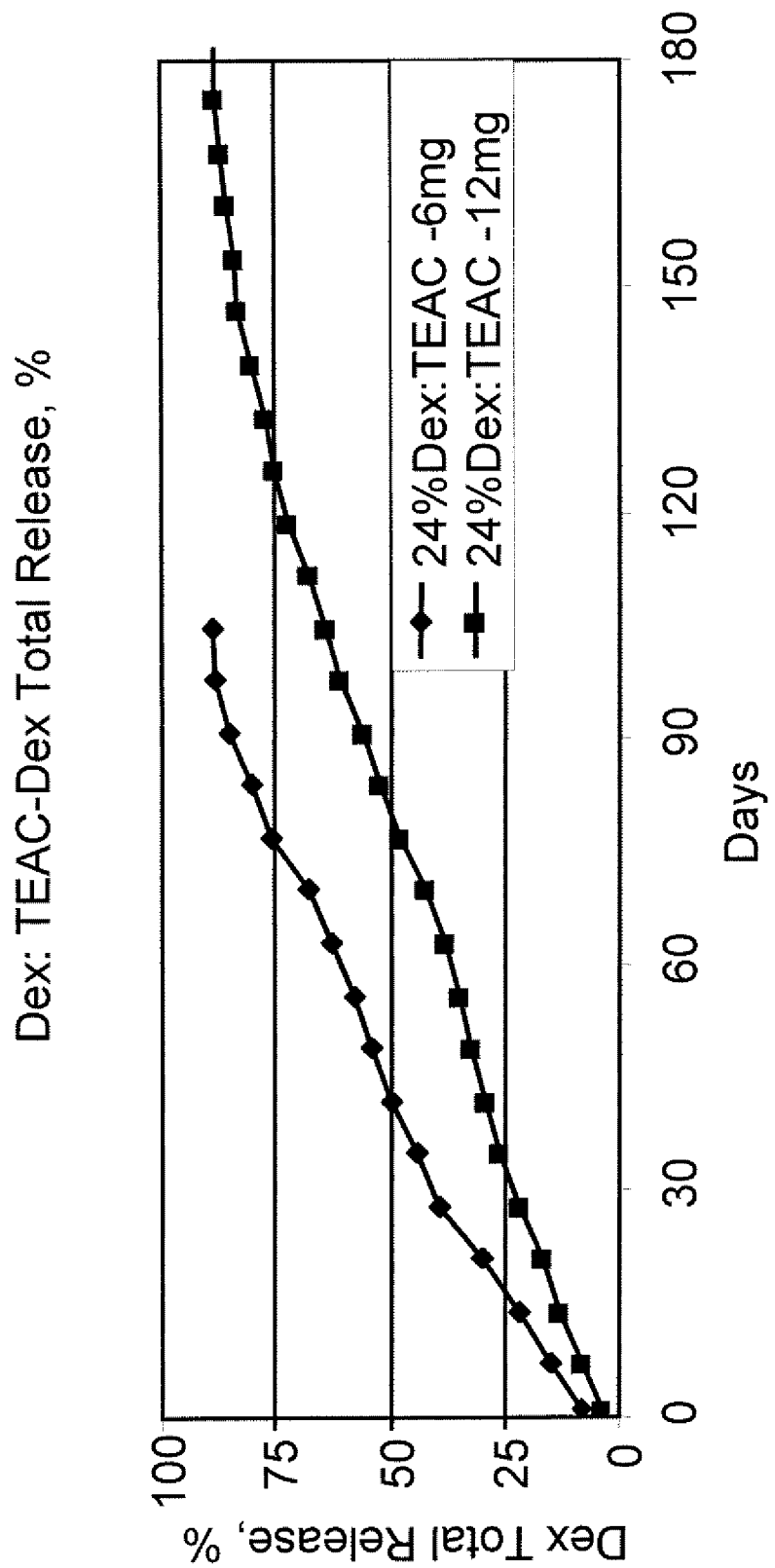
FIG. 6 depicts the percent Dex released in vitro from a formulation of 24% Dex and Triethyl O-Acetyl Citrate (TEAC).
Figure 7:
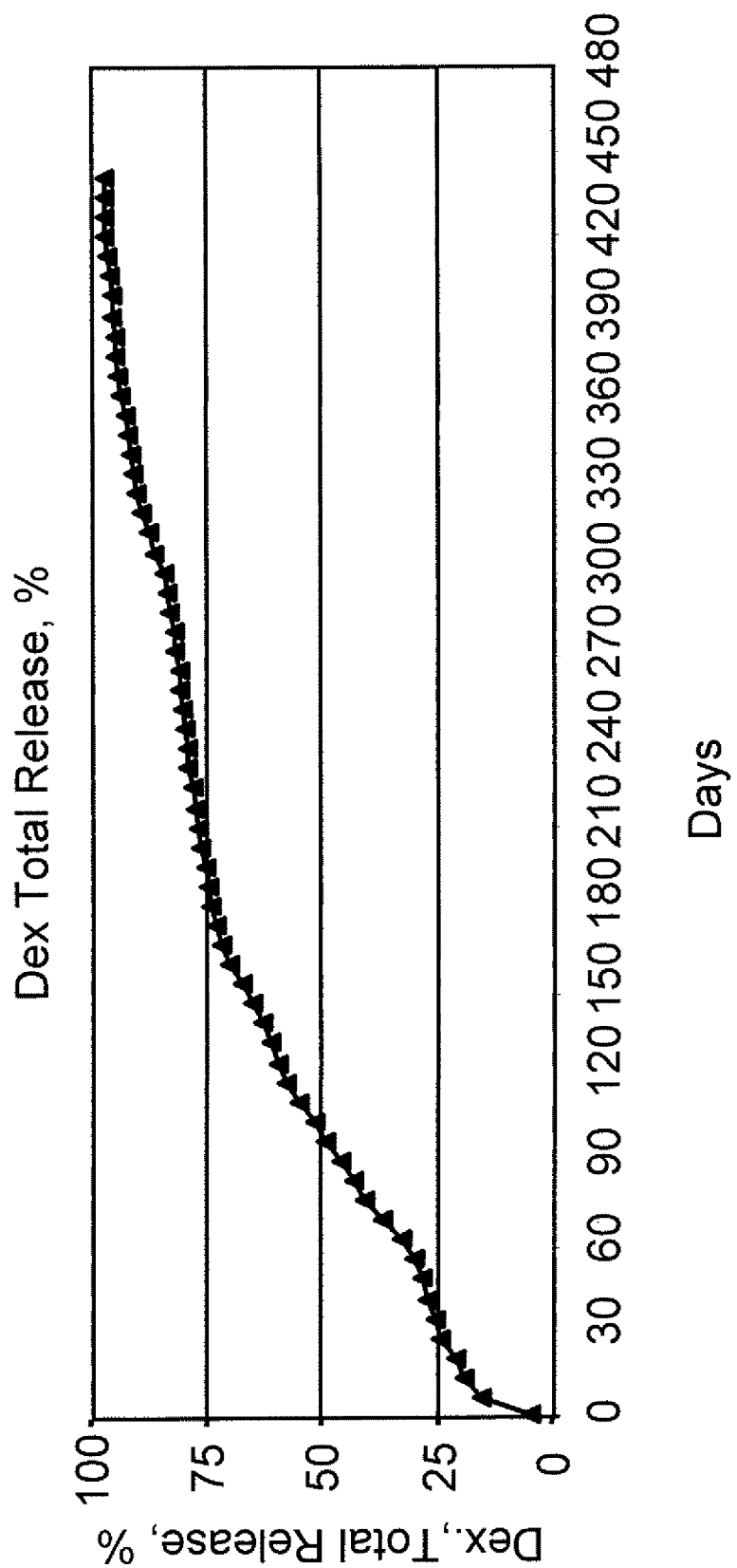
FIG. 7 shows the percent Dex released in vitro from a formulation of 20% Dex and TEAC/Tocopheryl acetate.

To 760 mg of TEAC was added 240 mg of Dexamethasone with ample stirring to form a homogeneous mixture, Six mg (25 μl) and 12 mg (25 μl) microdrops of this mixture were each incubated in 10 ml of 0.9% saline at 37° C. Periodically, 8 ml portions were withdrawn for assaying and replaced with 8 ml of fresh 0.9% saline. The release of Dex from a formulation consisting of 24% Dex in TEAC is depicted in FIG. 6. The release of Dex from a formulation consisting of a 6 mg (25 μl) microdrop of 20% Dex in 1:1 TEAC/Tocopheryl acetate is reflected in FIG. 7. In summary, these results indicate that adding tocopheryl acetate to the TEAC excipient can extend the sustained release of therapeutic levels of Dex up to 450 days.

Modifications of the above described modes for carrying out the invention that are obvious to those of ordinary skill in the surgical, pharmaceutical, or related arts are intended to be within the scope of the appended claims.

We claim:

1. A method of lowering intraocular pressure in a subject comprising the step of: administering to the eye of a subject in need thereof an eye drop formulation consisting of prostaglandin dissolved, dispersed or suspended in tocopheryl acetate; wherein the administration of a unit dose of a single eye drop has therapeutic effect for seven days and administration is repeated only once every seven days.

2. A pharmaceutical eye drops formulation for lowering intraocular pressure consisting of timolol dissolved, dispersed or suspended in tocopheryl acetate; wherein a unit dosage of one drop provides sustained release of timolol for seven days.

3. A method of lowering intraocular pressure in a subject comprising the step of: administering to the eye of a subject in need thereof an eye drop consisting of timolol dissolved, dispersed or suspended in tocopheryl acetate; and wherein the administration of a unit dose of a single drop has therapeutic effect for seven days and administration is repeated only once every seven days.

4. A pharmaceutical eye drops formulation for lowering intraocular pressure consisting of prostaglandin dissolved, disperse or suspended in tocopheryl acetate; wherein a dosage unit of a single drop provides sustained release of said prostaglandin for seven days.

5. A dosage dispensing container comprising the pharmaceutical eye drops formulation of claim 2.

6. A dosage dispensing container comprising the pharmaceutical eye drops formulation of claim 4.

* * * * *

UNITED STATES PATENT AND TRADEMARK OFFICE
CERTIFICATE OF CORRECTION

PATENT NO.       : 8,541,413 B2  
APPLICATION NO.  : 12/236877  
DATED            : September 24, 2013  
INVENTOR(S)      : Vernon G. Wong and Louis L. Wood Page 1 of 1

It is certified that error appears in the above-identified patent and that said Letters Patent is hereby corrected as shown below:

Under the Related U.S. Application date on the title page column 1:

Item (60), please correct provisional application No. "60/690,315, 06/14/2005" to read as follows:

--60/960,315, 09/25/2007--.

Signed and Sealed this  
Tenth Day of December, 2013

Margaret A. Focarino  
*Commissioner for Patents of the United States Patent and Trademark Office*